US 7,037,510 B2

(12) United States Patent
Andersen et al.

(10) Patent No.: US 7,037,510 B2
(45) Date of Patent: May 2, 2006

(54) HYBRIDS OF M. TUBERCULOSIS ANTIGENS

(75) Inventors: Peter Andersen, Brønshøj (DK); Anja Weinreich Olsen, Søborg (DK); Rikke Louise Vinther Skjøt, Hedehusene (DK); Peter Birk Rasmussen, Frederiksberg (DK)

(73) Assignee: Statens Serum Institut, Copenhagen S. (DK)

( * ) Notice: Subject to any disclaimer, the term of this patent is extended or adjusted under 35 U.S.C. 154(b) by 394 days.

(21) Appl. No.: 09/805,427

(22) Filed: Mar. 13, 2001

(65) Prior Publication Data

US 2002/0176867 A1 Nov. 28, 2002

Related U.S. Application Data

(63) Continuation-in-part of application No. 09/246,191, filed on Dec. 30, 1998, now abandoned.
(60) Provisional application No. 60/070,488, filed on Jan. 5, 1998, and provisional application No. 60/044,624, filed on Apr. 18, 1997.

(30) Foreign Application Priority Data

Nov. 10, 1997 (DK) .......................... 1997 01277

(51) Int. Cl.
*A61K 39/04* (2006.01)
*A61K 39/00* (2006.01)
*A61K 49/00* (2006.01)

(52) U.S. Cl. ...................... 424/248.1; 424/9.1; 424/9.2; 424/93.2; 424/184.1; 424/185.1; 424/190.1; 424/192.1; 424/200.1; 424/234.1; 424/257.1; 424/278.1; 435/41; 435/69.1; 435/69.3; 435/71.1; 435/252.1; 435/253.1; 435/440; 530/300; 530/350; 536/23.1; 536/23.7

(58) Field of Classification Search .................. 424/9.1, 424/9.2, 184.1, 185.1, 190.1, 192.1, 200.1, 424/93.1, 234.1, 93.2, 248.1, 257.1, 278.1; 435/41, 69.1, 69.3, 71.1, 440, 252.1, 253.1; 530/300, 350, 23.1, 23.7; 536/23.1, 23.7
See application file for complete search history.

(56) References Cited

U.S. PATENT DOCUMENTS

| 4,683,578 A | 7/1987 | Betts et al. |
| 4,891,315 A | 1/1990 | Watson et al. |
| 4,952,395 A | 8/1990 | Shinnick et al. |
| 4,976,958 A | 12/1990 | Shinnick et al. |
| 5,026,546 A | 6/1991 | Hilgers et al. |
| 5,330,754 A | 7/1994 | Kapoor et al. |
| 5,559,011 A | 9/1996 | Kapoor et al. |
| 5,955,077 A | 9/1999 | Andersen et al. |

FOREIGN PATENT DOCUMENTS

| DE | 195 40 250 | 2/1997 |
| EP | 0 729 250 | 8/1996 |
| EP | 0 734 132 | 9/1996 |
| EP | 0 869 649 | 10/1998 |
| WO | WO 92 14823 | 9/1992 |
| WO | WO 95/01441 | 1/1995 |
| WO | WO 96/37219 | 11/1996 |
| WO | WO 97/09428 | 3/1997 |
| WO | WO 97/09429 | 3/1997 |
| WO | WO 98 44119 | 10/1998 |
| WO | WO 98 53075 | 11/1998 |
| WO | WO 98 53076 | 11/1998 |

OTHER PUBLICATIONS

Wiegeshaus, E.H., eta al "Evaluation of the protective potency of a new tuberculosis vaccines", Reviews of Infectious Diseases, vol. 11, Suppl. 2, pp. S484–S490, Mar. 1989.*
Andersen, P. et al., Jun. 1991, Proteins released from Mycobacterium Tuberculosis during growth, Infect. Immun. 59(6): 1905–1910.
Baldwin, S.L. et al., Jun. 1998, Evaluation of new vaccines in the mouse and guinea pig model of tuberculosis, Infect. Immun. 66(6):2951–2959.
Boesen, H. et al., Apr. 1995, Human T–cell responses to secreted antigen fractions of Mycobacterium tuberculosis, Infect. Immun. 63(4): 1491–1497.
Brandt et al., 1996, Key epitopes on the ESAT–6 antigen recognized in mice during the recall of protective immunity to Mycobacterium tuberculosis, J. Immunol. 157:3527–3533.
Brandt L. et al., Feb. 2000, ESAT–6 subunit vaccination against Mycobacterium tuberculosis, Infect. Immun. 68:791–795.
Cole, S.T. et al, Jun. 1998, Deciphering the biology of Mycobacterium tuberculosis from the complete genome sequence, Nature 393:537–544.
Horwitz et al., Feb. 1995, Protective immunity against tuberculosis induced by vaccination with major extracellular proteins of Mycobacterium tuberculosis, Proc. Natl. Acad. Sci.USA.92:1530–1534.
Olsen A.W. et al., Jun. 2000, Efficient protection against Mycobacterium tuberculosis by vaccination with a single subdominant epitope from the ESAT–6 antigen, Eur J. Immunol. 30(6):1724–1732.

(Continued)

*Primary Examiner*—Rodney P Swartz
(74) *Attorney, Agent, or Firm*—Thomas J. Kowalski; Angela M. Collison; Frommer Lawrence & Haug LLP

(57) ABSTRACT

The present invention discloses fusion proteins of the immunodominant antigens ESAT-6 and Ag85B from *Mycobacterium tuberculosis* or homologues thereof, and a tuberculosis vaccine based on the fusion proteins, which vaccine induces efficient immunological memory.

21 Claims, 10 Drawing Sheets

OTHER PUBLICATIONS

Figure 1:
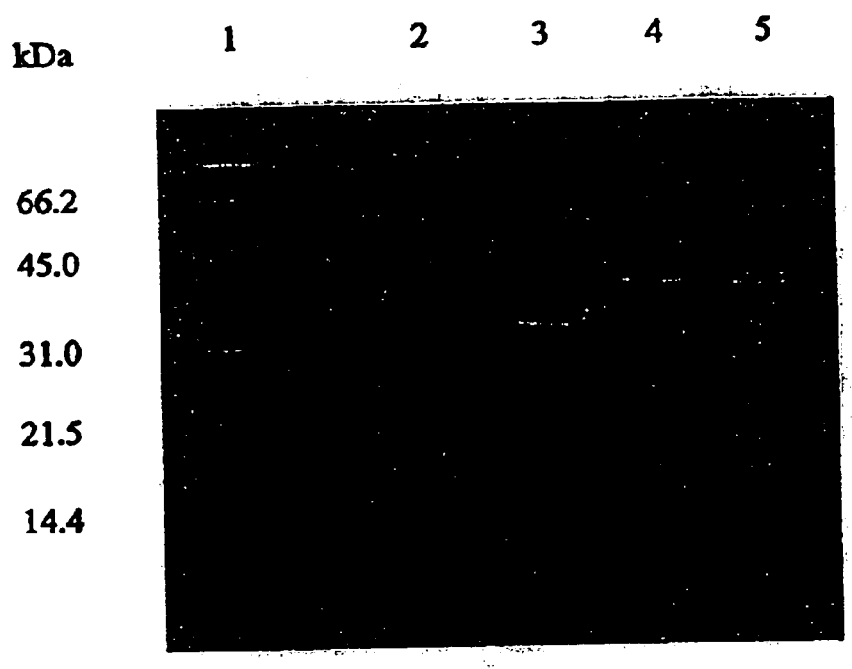

Ravn, P. et al., Mar. 1999, Human T Cell response to ESAT-6 antigen from Mycobacterium tuberculosis, J. Infect. Dis. 179:637-645.
Roche, P.W. et al. Dec. 1994, T-cell determinants and antibody binding sites on the major mycobacterial secretory protein MPB59 of Mycobacterium bovis, Infect. Immun.62(12):5319-5326.
Rosenkrands, I., et al., Identification and characterization of a 29-kilodalton protein from Mycobacterium tuberculosis culture filtrate recognized by mouse memory effector cells, Infect. Immun 66(6); 2728-2735.
Skjøt, R.L.V., et al., Jan. 2000, Comparative evaluation of low-molecular-mass proteins from Mycobacterium tuberculosis identifies members of the ESAT-6 family as immunodominant T-cell antigens, Infect. Immun. 68(1):214-220.
Stryhn, A., et al., 1996, Peptide binding specificity of major histocompatibility complex class I resolved into an array of apparently independent subspecificites: quantitation by peptide libraries and improved prediction of binding, Eur. J. Immunol. 26:1911-1918.
Ulrichs, T. et al. , 1998, Differential T cell responses to Mycobacterium tuberculosis ESAT6 in tuberculosis patients and healthy donors, Eur. J. Immunol. 28:3949-3958.
P. Andersen et al., Identification of Immunodominant antigens during infection with mycobacterium tuberculosis, J. Immunol, 36, 823-831, 1992.
Peter Andersen et al., Proteins released from mycobacterium tuberculosis during growth, Infection and Immunity, Jun. 1991, vol. 59, No. 6, p. 1905-1910.
Peter Andersen et al., Specificity of a protective memory immune response against mycobacterium tuberculosis, Infection and Immunity, Mar. 1993, vol. 61, No. 3, p. 844-851.
Peter Andersen et al., T-cell proliferatiive response to antigens secreted by mycobacterium tuberculosis, Infection and Immunity, Apr. 1991, vol. 59, No. 4, p. 1558-1563.
Kris Huygen et al., Spleen cell cytokine secretion in mycobacterium bovis BCG-infected mice, infection and immunity, Jul. 1992, vol. 60, No. 7, p. 2880-2886.
Christine Abou-Zeid et al., Characterization of fibronectin-binding antigens released by mycobacterium tuberculosis and mycobacterium bovis BCG, Infection and Immunity, Dec. 1988, vol. 56, No. 12, p. 3046-3051.
Martine Borremans et al., Cloning sequence determination, and expression of a 32- kilodalton-protein gene of mycobacterium tuberculosis, Infection and Immunity, Oct. 1989, vol. 57, No. 10, p. 3123-3130.
Peter Andersen, Effective vaccination of mice against mycobacterium tuberculosis infection with a soluble mixture of secreted mycobacterial proteins, Infection and Immunity, Jun. 1994, vol. 62, No. 6.
Nagai et al., Isolation and partial characterization of major protein antigens in the culture fluid of mycobacterium tuberculosis, Infection and Immunity, Jan. 1991, vol. 59, No. 1, p. 372-382.
Borodovsky et al., Computers Chem., vol. 17, pp. 123-133.
Brown, EMBL Sequence database.
Harboe et al., Infect. Immun. vol. 64, pp. 16-22.
Von Heijne et al., J. Mol. Biol., vol. 173, pp. 243-251.
Hochstrasser et al., Annal Biochem., vol. 173, pp. 424-435.
Kohler et al., Nature, vol. 256, pp. 495-497.
Li et al., Infect. Immun., vol. 61, pp. 1730-1734.
Lindblad et al., Infect. Immun., vol. 65, pp. 623-629.
Mahairs et al., J. Bacteriol., vol. 178, pp. 1274-1282.
Nagai et al., Infect. Immun., vol. 59, pp. 372-382.
Oettinger et al., Infect. Immun., vol. 62, pp. 2058-2064.
Ohara et al., Scand. J. Immunol., vol. 41, pp. 433-442.
Pal et al., Infect. Immun., vol. 60, pp. 4781-4792.
Pearson et al., Proc. Natl. Acad. Sci., USA, vol. 85, pp. 2444-2448.
Ploug et al., Anal Biochem., vol. 181, pp. 33-39.
Porath et al., FEBS Lett., vol. 185, pp. 306-310.
Roberts et al., Immunol., vol. 85, pp. 502-508.
Rosenkrands et al., Infect. Immun., vol. 66, No. 6, pp. 2728-2735.
Andersen et al., J. Immunol. vol. 154, pp. 3359-3372.
Rosenkrands et al., EMBL: Y12820.
Sorensen et al., Infect. Immun., vol. 63, pp. 1710-1717.
Theisen et al., Clinical and Diagnostic Laboratory Immunology, vol. 2, pp. 30-34.
Valdes-Stauber et al., Appl. Environ. Microbiol., vol. 60, pp. 3809-3814.
Valdes-Stauber et al., Appl. Environ. Microbiol., vol. 62, No. 4, pp. 1283-1286.
Williams, Science, 272:27.
Young et al., Proc. Natl. Acad. Sci. USA, vol. 82, pp. 2583-2587.
Crabtree, et al., EMBL Sequence database.
Van Dyke et al., Gene, pp. 99-104.
Gosselin et al., J. Immunol., vol. 149, pp. 3477-3481.
XP002092185 EMBL Sequence.
Andersen et al., J. Immunol. Methods, vol. 161, pp. 29-39.
Andersen et al., Infect. Immun., vol. 60, pp. 2317-2323.
Rosenkrands et al., EMBL: 007812.
Wiegeshaus, E.H., et al. "Evaluation of the Protective Protency of New Tuberculosis Vaccines", Reviews of Infectious Diseases, vol. 11, supplement 2, pp. S484-S490, Mar. 1989.
Orme, I.M., "New Vaccines against Tuberculosis", Infectious Disease Clinic of North America, vol. 13, No. 1, pp. 169-185, Mar. 1999.
Andersen, Infect. Immun. vol. 62, pp. 2536-2544.
Barkholt et al., Anal. Biochem., vol. 177, pp. 318-322.
Scandinavian Journal of Immunology vol. 36, 1992 pp. 823-831 P. Andersen et al. 'Identification of immunodominant antigens during infection with Mycobacterium tuberculosis'.
Infection and Immunity vol. 61, No. 3, Mar. 1993, Washington US pp. 844-851 Peter Andersen et al. 'Specificity of a protective memory immune response against Mycobacterium tuberculosis'.
Infection and Immunity vol. 59, No. 4, Apr. 1991, Washington US pp. 1558-1563 Peter Andersen et al. 'T-cell proliferative response to antigens secreted by Mycobacterium tuberculosis' cited in the application.
Infection and Immunity vol. 60, No. 7, Jul. 1992, Washington US pp. 2880-2886 Kris Huygen et al. 'Spleen cell cytokine secretion in Mycobacterium bovis BCG-infected mice'.
Infection and Immunity vol. 59, No. 6, Jun. 1991, Washington US pp. 1905-1910 Peter Andersen et al. 'Proteins released from Mycobacterium tuberculosis during growth' cited in the application.
Infection and Immunity vol. 56, No. 12, Dec. 1988, Washington US pp. 3046-3051 Christiane Abou-Zeid et al. 'Characterization of fibronectin-binding antigens released by Mycobacterium toberculosis and Mycobacterium bovis BCG'.

Infection and Immunity vol. 57, No. 10, Oct. 1989, Washington US pp. 3123–3130 Martine Borremans et al. 'Cloning sequence determination, and expression of a 32–kilodalton–protein gene of Mycobacterium tuberculosis'.

Infection and Immunity vol. 62, No. 6, Jun. 1994, Washington US pp. 2536–2544 Peter Andersen 'Effective vaccination of mice against Mycobacterium tuberculosis infection with a soluble mixture of secreted mycobacterial proteins'.

Moriyama S et al.: "Digital Transmission of High Bit Rate Signals Using 16DAPSK–OFDM Modulation Scheme" IEEE Transactions on Broadcasting, Mar. 1998, vol. 44, No. 1, pp. 115–122, XP002105431.

Man et al. "Treatment of human muscle creatine kinase with glutaraldehyde prefenentially increases the immunogenicity of the native conformation and permits production of high–affinity monoclonal antibodies which recognize two distinct surface epitopes", J, Oct. 1, 1989.

A.B. Andersen et al., MPB64 Possesses Tuberculosis–Complex'–Specific B– and T–Cell Epitopes, Scand J. Immunol 34, 365–372, 1991.

Anne Worsaee et al., Allergenic and Blastogenic Reactivity of Three Antigens from Mycobacterium tuberculosis in Sensitized Guinea Pigs, Infection and Immunity, Dec. 1987, p 2922–2927.

Yamaguchi Ryugi, et al., "Cloning and Characterization of the Gene for immunogenic Protein MPB64 of Mycobacterium bovis BCG" Infection and Immunity 57(1):283–288 (1989).

Wiker, H.G., et al., "A Family of Cross–Reacting Proteins Secreted by Mycobacterium tuberculosis", Scand J. Immunol. 36:307–319 (1992).

Leao, S.C., "Tuberculosis: New Strategies for the Development of Diagnostic Tests and Vaccines", Brazilian J. Med. Biol. Res. 26:827–833 (1993).

Oettiner, Thomas, et al., " Cloning and B–Cell–Epitope Mapping of MPT64 from Mycobacterium tuberculosis H37Rv", Infection and Immunity 62(5):2058–2064 (1994).

Boswell et al. Computational Molecular Biology, Oxford University Press, pp. 161–178, 1988.

Flesch and Kaufmann, Mycobacterial Growth Inhibition by Inteferon–y–Activated Bone Marrow Macrophages and Differential . . . tuberculosis, The Journal of Immunology, vol. 138, No. 12, pp. 4408–4413, Jun. 15, 1987.

Lefford and McGregor, Immunological Memory in Tuberculosis, Cellular Immunology, vol. 14, pp. 417–428, 1974.

Orme, Characteristics and Specificity of Acquired Immunologic Memory to Mycobacterium tuberculosis Infection The Journal of Immunology, vol. 140, No. 10, pp. 3589–3593, May 15, 1988.

G.A.W. Rock, The Role of Activated Macrophages in protection and immunopathology in Tuberculosis, Research in Microbiology vol. 141, No. 2, Feb. 1990, pp. 253–256.

Sanger, Nicklen and Coulson, DNA Sequencing with Chain– Terminating Inhibitors, Proc. Nat. Acad. Sci USA, vol. 74, No. 12, pp. 5463–5467, Dec. 1977.

Young, Bloom, Grosskinsky, Ivanyi, Thomas and Davis, Dissection of Mycobacterium Tuberculosis antigens Using recombinant DNA, Proc. Natl. Acad. Sci. USA, vol. 82, pp 2583–2587, May 1985.

Kaufman (Microbiological Sciences 4 (11) Nov. 1987 pp. 324–328).

Lazar et al. (Molecular & Cellular Bio. Mar. 1988 pp. 1247–1252).

Burgess et al (J. of Cell Biology vol. III Nov. 1990 pp. 2129–2138).

Salgaller et al. (Cancer Immuno. Immuother. (1994) vol. 39 pp. 105–116).

Walsh, G.P. et al., "The Philippine cnymolgus mondey (*Macaca fasicularis*) provides a new nonhuman primate model of tuberculosis that resembles human disease." Nature Medicine 2(4):430–436, Apr. 1996.

* cited by examiner

HYBRIDS OF M. TUBERCULOSIS ANTIGENS

RELATED APPLICATIONS

This application is a continuation-in-part of U.S. Ser. No. 09/246,191, filed Dec. 30, 1998, which claims priority from U.S. provisional application 60/070,488, filed 5 Jan. 1998. Reference is also made to: the concurrently-filed U.S. application of Andersen et al., Ser. No. 09/804,980; U.S. application Ser. No. 09/289,388 filed 12 Apr. 1999, which is a continuation of U.S. application Ser. No. 08/465,640 filed 5 Jun. 1995, now U.S. Pat. No. 5,955,077, issued Sep. 21, 1999, which is a continuation-in-part of U.S. Ser. No. 08/123,182 filed 20 Sep. 1993, now abandoned, and a continuation-in-part of PCT/DK94/00270, filed Jul. 1, 1994, published as WO95/01441, and claiming priority from Danish application 0798/93, filed Jul. 2, 1993;U.S. application Ser. No. 09/050,739 filed 30 Mar. 1998, which is claims priority from U.S. provisional application Ser. No. 60/044,624 filed 18 Apr. 1997; Andersen et al., application Ser. No. 09/791,171, filed 20 Feb. 2001, as a divisional of U.S. application Ser. No. 09/050,739; and commonly-owned U.S. Pat. No. 6,120,776.

Each of these patents, patent applications and patent publications, as well as all documents cited in the text of this application, and references cited in the documents referred to in this application (including references cited in the aforementioned patents, patent applications and patent publications or during their prosecution) are hereby incorporated herein by reference.

FIELD OF INVENTION

The present application discloses new fusion proteins of the immunodominant antigens ESAT-6 and Ag85B from *Mycobacterium tuberculosis* or homologues thereof, and a tuberculosis subunit vaccine comprising at least one fusion protein. The vaccine induced efficient immunological memory.

GENERAL BACKGROUND

Human tuberculosis caused by *Mycobacterium tuberculosis* (*M. tuberculosis*) is a severe global health problem, responsible for approx. 3 million deaths annually, according to the WHO. The worldwide incidence of new tuberculosis (TB) cases had been falling during the 1960s and 1970s but during recent years this trend has markedly changed in part due to the advent of AIDS and the appearance of multidrug resistant strains of *M. tuberculosis*.

The only vaccine presently available for clinical use is BCG, a vaccine whose efficacy remains a matter of controversy. BCG generally induces a high level of acquired resistance in animal models of TB, but several human trials in developing countries have failed to demonstrate significant protection. Notably, BCG is not approved by the FDA for use in the United States because BCG vaccination impairs the specificity of the Tuberculin skin test for diagnosis of TB infection.

This makes the development of a new and improved vaccine against TB an urgent matter, which has been given a very high priority by the WHO. Many attempts to define protective mycobacterial substances have been made, and different investigators have reported increased resistance after experimental vaccination. However, the demonstration of a specific long-term protective immune response with the potency of BCG has not yet been achieved.

Immunity to *M. tuberculosis* is characterized by some basic features; specifically sensitized T lymphocytes mediates protection, and the most important mediator molecule seems to be interferon gamma (IFN-$\gamma$).

*M. tuberculosis* holds, as well as secretes, several proteins of potential relevance for the generation of a new TB vaccine. For a number of years, a major effort has been put into the identification of new protective antigens for the development of a novel vaccine against TB. The search for candidate molecules has primarily focused on proteins released from dividing bacteria. Despite the characterization of a large number of such proteins only a few of these have been demonstrated to induce a protective immune response as subunit vaccines in animal models, most notably ESAT-6 and Ag85B, also called MPT59 (Brandt et al 2000).

Animal tuberculosis is caused by *Mycobacterium bovis*, which is closely related to *M. tuberculosis* and within the tuberculosis complex. *M bovis* is an important pathogen that can infect a range of hosts, including cattle and humans. Tuberculosis in cattle is a major cause of economic loss and represents a significant cause of zoonotic infection. A number of strategies have been employed against bovine TB, but the approach has generally been based on government organized programs by which animals deemed positive to defined screening test are slaughtered.

Alternative strategies in TB vaccine development such as subunit vaccines (Andersen, P. 1994, Horwitz et al 1995, Roberts, A. D. et al 1995), genetic immunization (Huygen et al 1996, Tascon et al 1996) and attenuated strains of *M. tuberculosis* (Guleria et al 1996) are currently being explored in many laboratories. Due to the complexity of the host immune response against tuberculosis and the genetic restriction imposed by major histocompatibility complex molecules (MHC), it has become clear that an effective subunit vaccine containing multiple epitopes may be required to ensure a broad coverage of a genetically heterogeneous population. The present inventors and others have previously demonstrated that vaccines based on a mixture of culture filtrate antigens can induce levels of protection similar to BCG in mice (Andersen, P. 1994, Horwitz et al 1995, Roberts, A. D. et al 1995), but so far only a few experimental vaccines based on a single antigen have proved successful in animal models (Brandt at al 2000, Huygen et al 1996, Tascon et al 1996).

SUMMARY OF THE INVENTION

In the present application the construction and initial immunological characterization of two recombinant fusion proteins between Ag85B and ESAT-6: ESAT-6-Ag85B and Ag85B-ESAT-6 is described. The most promising of these constructs, Ag85B-ESAT-6, being administered in the DDA/MPL adjuvant, provided a significant level of anti-TB protection expressed as a reduction of bacterial numbers in organs of mice challenged with *M. tuberculosis* by the aerosol or i.v route. There is a long held debate whether the bacterial load in various organs uniformly correlates with the ultimate outcome of tuberculosis infection, especially in animals vaccinated with experimental TB vaccines (Wiegeshaus, E. H. et al 1970, Baldwin, S. L. et al 1998).

Therefore, the present inventors have studied this vaccine in more detail and assessed both the mycobacterial burden in organs, the clinical development of disease and the survival time of vaccinated and subsequently challenged mice and guinea pigs.

In humans, HLA polymorphism is known to control the specificity of T cell responses to pathogens. Novel vaccine candidates, thus, need to be defined taking the polymorphism of the HLA molecule into consideration and, unlike whole organism-based vaccines, only a limited number of antigenic epitopes is exhibited to the immune system by mono- and oligoprotein vaccines. Here it is demonstrated that T cell lines derived from TB patients with various HLA genotypes broadly recognize Ag85B-ESAT-6 antigen, and that this subunit vaccine elicits immune responses against major T cell epitopes of these two antigens in the animal models.

As evidenced in the examples, the fusion polypeptide consisting of Ag85B fused N-terminally to ESAT-6 enhances the immunogenicity of ESAT-6 beyond what would be expected from the immunogenicities of Ag85B and ESAT-6 alone. The precise reason for this surprising finding is not yet known, but it is expected that either the presence of both antigens lead to a synergistic effect with respect to immunogenicity or the presence of a sequence N-terminally to the ESAT-6 sequence protects this immune dominant protein from loss of important epitopes known to be present in the N-terminus. A third, alternative, possibility is that the presence of a sequence C-terminally to the Ag85B sequence enhances the immunologic properties of this antigen.

Ag85B and ESAT-6 are both very promising vaccine candidate molecules for several reasons: i) they are strongly recognized T cell antigens in the first phase of infection (Brandt et al 1996, Ravn, P. et al 1999, Ulrichs, T. et al 1998); ii) they have demonstrated protective efficacy in animal models (Brandt et al 2000, Horwitz et al 1995, Tascon et al 1996); iii) they contain numerous well-characterized epitopes recognized in TB patients (Ravn, P. et al 1999, Roche, P. W. et al 1994, Ulrichs, T. et al 1998). The present inventors have demonstrated that a subunit vaccine based on a fusion protein of these molecules and the recently developed adjuvant for CMI responses DDA/MPL (Brandt et al 2000), induce levels of protective immunity similar to BCG in the mouse model of TB infection. One note of caution is, however, that the level of BCG protection monitored after the aerosol infection in this study (Table Ia, Exp. 1 and 2) is lower than reported before (Baldwin et al 1998, Delogu et al 2000, Li, Z et al. 1999). This difference may however be related to the route of challenge, because in the present study when using the i.v route high levels of protection were obtained with BCG (Table Ia, Exp. 3). Of interest in this regard, also in this experiment the protection induced by the fusion molecule was at the same level as BCG.

Recent international focus on TB vaccine research and the sequencing of the *M. tuberculosis* genome (Cole et al 1998) have resulted in the accelerated identification of novel mycobacterial proteins. Culture filtrates have attracted particular interest as a source of antigens, which elicit protective immune responses in various animal models of TB (Andersen, P. 1994, Baldwin et. 1998, Horwitz et al 1995, Roberts, A. D. et al 1995). Many of the recently identified proteins originate from culture filtrate such as ESAT-6 (Sorensen, A. L. et al 1995), TB 10.4 and CFP10 (Skjøt, R. L. V. et al 2000), MTB12 (Webb, J. R. et al 1998), MTB39 (Dillon et al 1999) and the APA (45/47 kDa) antigen (Dobos et al 1996). Human T cell responses to most of these antigens have been studied and compared to complex antigens such as tuberculin purified protein derivative (PPD) and ST-CF (Boesen et al 1995, Skjøt, R. L. V. et al 2000, Ulrichs, T. et al 1998). The data generated in these studies collectively demonstrate that even for the most immunodominant antigens described to date, a significant proportion of non-responders exist among donors responsive to PPD in vitro (Ravn, P. et al 1999, Skjøt, R. L. V. et al 2000). To ensure the necessary coverage of human populations with strongly recognized T cell epitopes, multi-component vaccines will therefore be necessary. Such vaccines will not necessarily have to contain a large number of different components as candidate antigens already exist which is recognized by a very high proportion of donors. In this regard, most of the analyses of human T cell recognition conducted so far have been based on PBMC cultures and more sensitive analyses will increase the percentage of responders as exemplified by the recent ELISPOT based evaluation of ESAT-6 recognition in TB patients where responses could be detected in more than 90% of the individuals tested (Pathan, A. et al 1998).

In addition to being more cost-effective and less time consuming, the delivery of these selected molecules as a single fusion protein has the potential advantage of inducing amplified responses to molecules with a low inherent immunogenicity. The present inventors have previously shown that ESAT-6 has a low inherent immunogenicity and requires a strong adjuvant such as DDA/MPL whereas no response to this molecule is found if ESAT-6 is provided in DDA alone (Brandt et al 2000). In this regard, a recent evaluation of immune responses induced by immunizing with the fusion protein in DDA have demonstrated that even in this mild adjuvant a very strong response to both ESAT-6 and Ag85B is found, indicating that the fusion to Ag85B may amplify the immune responses to a low immunogenic molecule like ESAT-6.

One of the preconditions for the successful implementation of any subunit vaccine as a possible replacement of BCG is the generation of long-term immunological memory. This point has been a particular cause of concern in TB subunit vaccine development and has been debated for years (Orme, I. M. et al 1993). This concern arose from the original observations that subunit vaccines based on killed mycobacterial cell wall preparations could induce high levels of immunity immediately after vaccination but that resistance waned rapidly over time (Anacker et al 1967). This was later demonstrated to be a consequence of the non-specific inflammatory response induced by these preparations (Orme, I. M. 1988). More recently a similar observation was made with findings of a rapid waning of specific immunity after vaccination with experimental vaccines based on culture filtrate proteins and IFA (Roberts, A. D. et al 1995). In this study the resistance to TB was almost down at prevaccination levels 150 days post-vaccination. Based on such findings it has been anticipated that a continuous antigen exposure provided by a live vaccine such as BCG would be necessary for the maintenance of efficient immunological memory. In contrast to the findings described above the subunit vaccine of the present invention induced high levels of protection throughout the observation period and somewhat surprisingly the tendency was that the immunity reached higher levels at day 210 than at day 70. At this late time point, the subunit vaccine even exceeded the immunity expressed in the lung after BCG vaccination. Although the reason for this high activity is presently not clear, the DDA component of the adjuvant in addition to be highly stimulatory, may act as a depot for antigen by the formation of micelles with a slow but sustained release of antigen. That DDA may have this activity would be in agreement with the original observation of high levels of specific protective T cells which could adoptively transfer immunity to recipient mice as late as 22 weeks after vaccination with a mixture of DDA and *M. tuberculosis* culture filtrate (Andersen, P. 1994)

In conclusion, it is clearly demonstrated that a subunit vaccine based on a fusion protein between Ag85B and ESAT-6 is able to induce efficient long-term memory immunity highly protective against TB in the aerosol mouse model. Together with results that illustrate that the fusion between Ag85B and ESAT-6 induces protection in guinea pigs and in primates these results will hopefully lay the ground for introducing such vaccines as a realistic alternative to BCG in the near future.

DETAILED DISCLOSURE

Hence, one embodiment of the invention pertains to a fusion polypeptide which comprises a first amino acid sequence including at least one stretch of amino acids constituting a T-cell epitope derived from the *M tuberculosis* protein ESAT-6 (SEQ ID NO: 1), and a second amino acid sequence including at least one stretch of amino acids constituting a T-cell epitope derived from the *M tuberculosis* protein Ag85B and/or a stretch of amino acids which protects the first amino acid sequence from in vivo degradation or post-translational processing (SEQ ID NO: 2). The first amino acid sequence may be situated N- or C-terminally to the second amino acid sequence, but in line with the above considerations regarding protection of the ESAT-6 N-terminus, it is preferred that the first amino acid sequence is C-terminal to the second.

It is preferred that the amino acid sequences of the first and second T-cell epitopes each have a sequence identity of at least 70% with the natively occurring sequence in the proteins from which they are derived and it is even further preferred that the entire first and/or second amino acid sequence has a sequence identity of at least 70% with the amino acid sequence of the protein from which they are derived.

In a presently most preferred embodiment, the fusion polypeptide comprises ESAT-6 fused to Ag85B wherein ESAT-6 is fused to the C-terminus of Ag85B. In one special embodiment, there are no linkers introduced between the two amino acid sequences constituting the two parent polypeptide fragments.

Definitions

The word "polypeptide" in the present specification and claims should have its usual meaning. That is an amino acid chain of any length, including a full-length protein, oligopeptides, short peptides and fragments thereof, wherein the amino acid residues are linked by covalent peptide bonds.

The polypeptide may be chemically modified by being glycosylated, by being lipidated (e.g. by chemical lipidation with palmitoyloxy succinimide as described by Mowat et al. 1991 or with dodecanoyl chloride as described by Lustig et al. 1976), by comprising prosthetic groups, or by containing additional amino acids such as e.g. a his-tag or a signal peptide.

Each polypeptide may thus be characterized by comprising specific amino acid sequences and be encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptide and still be immunogenic in any of the biological assays described herein. Substitutions are preferably "conservative". These are defined according to the following table. Amino acids in the same block in the second column and preferably in the same line in the third column may be substituted for each other. The amino acids in the third column are indicated in one-letter code.

| ALIPHATIC | Non-polar | GAP |
| --- | --- | --- |
|  |  | ILV |
|  | Polar-uncharged | CSTM |
|  |  | NQ |
|  | Polar-charged | DE |
|  |  | KR |
| AROMATIC |  | HFWY |

A preferred polypeptide within the present invention is an immunogenic antigen from *M. tuberculosis*. Such antigen can for example be derived from *M. tuberculosis* and/or *M. tuberculosis* culture filtrate. Thus, a polypeptide comprising an immunogenic portion of one of the above antigens may consist entirely of the immunogenic portion, or may contain additional sequences. The additional sequences may be derived from the native *M. tuberculosis* antigen or be heterologous and such sequences may, but need not, be immunogenic.

Each polypeptide is encoded by a specific nucleic acid sequence. It will be understood that such sequences include analogues and variants hereof wherein such nucleic acid sequences have been modified by substitution, insertion, addition or deletion of one or more nucleic acids. Substitutions are preferably silent substitutions in the codon usage which will not lead to any change in the amino acid sequence, but may be introduced to enhance the expression of the protein.

In the present context the term "substantially pure polypeptide" means a polypeptide preparation which contains at most 5% by weight of other polypeptide material with which it is natively associated (lower percentages of other polypeptide material are preferred, e.g. at most 4%, at most 3%, at most 2%, at most 1%, and at most ½%). It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at least 99,25%, at least 99,5%, and at least 99,75%. It is especially preferred that the polypeptide is in "essentially pure form", i.e. that the polypeptide is essentially free of any other antigen with which it is natively associated, i.e. free of any other antigen from bacteria belonging to the tuberculosis complex or a virulent mycobacterium. This can be accomplished by preparing the polypeptide by means of recombinant methods in a non-mycobacterial host cell as will be described in detail below, or by synthesizing the polypeptide by the well-known methods of solid or liquid phase peptide synthesis, e.g. by the method described by Merrifield or variations thereof.

By the term "virulent mycobacterium" is understood a bacterium capable of causing the tuberculosis disease in an animal or in a human being. Examples of virulent mycobacteria are *M. tuberculosis, M. africanum,* and *M. bovis*. Examples of relevant animals are cattle, possums, badgers and kangaroos.

By "a TB patient" is understood an individual with culture or microscopically proven infection with virulent mycobacteria, and/or an individual clinically diagnosed with TB and who is responsive to anti-TB chemotherapy. Culture, microscopy and clinical diagnosis of TB are well known by any person skilled in the art.

By the term "PPD-positive individual" is understood an individual with a positive Mantoux test or an individual where PPD induces a positive in vitro recall response determined by release of IFN-γ.

By the term "delayed type hypersensitivity reaction" (DTH) is understood a T-cell mediated inflammatory response elicited after the injection of a polypeptide into, or application to, the skin, said inflammatory response appearing 72–96 hours after the polypeptide injection or application.

By the term "IFN-γ" is understood interferon-gamma. The measurement of IFN-γ is used as an indication of an immunological response.

By the terms "nucleic acid fragment" and "nucleic acid sequence" is understood any nucleic acid molecule including DNA, RNA, LNA (locked nucleic acids), PNA, RNA, dsRNA and RNA-DNA-hybrids. Also included are nucleic acid molecules comprising non-naturally occurring nucleosides. The terms include nucleic acid molecules of any length e.g. from 10 to 10000 nucleotides, depending on the use. When the nucleic acid molecule is for use as a pharmaceutical, e.g. in DNA therapy, or for use in a method for producing a polypeptide according to the invention, a molecule encoding at least one epitope is preferably used, having a length from about 18 to about 1000 nucleotides, the molecule being optionally inserted into a vector. When the nucleic acid molecule is used as a probe, as a primer or in antisense therapy, a molecule having a length of 10–100 is preferably used. According to the invention, other molecule lengths can be used, for instance a molecule having at least 12, 15, 21, 24, 27, 30, 33, 36, 39, 42, 50, 60, 70, 80, 90, 100, 200, 300, 400, 500 or 1000 nucleotides (or nucleotide derivatives), or a molecule having at most 10000, 5000, 4000, 3000, 2000, 1000, 700, 500, 400, 300, 200, 100, 50, 40, 30 or 20 nucleotides (or nucleotide derivatives).

The term "stringent" when used in conjunction with nucleic acid hybridization conditions is as defined in the art, i.e. the hybridization is performed at a temperature not more than 15–20° C. under the melting point Tm, cf. Sambrook et al, 1989, pages 11.45–11.49. Preferably, the conditions are "highly stringent", i.e. 5–10° C. under the melting point Tm.

By the term "linker sequence" is understood any molecule being able to fuse the antigens. The term encompasses molecules being able to react with both the antigens, e.g. fusing the antigens C-terminal to N-terminal, N-terminal to N-terminal or C-terminal to C-terminal. Although such terminal fusions are presently preferred, the term also encompasses linkers binding to other parts of the antigens. Examples of molecules being able to fuse the antigens N-terminal to N-terminal is a molecule with two or more groups that are able to form a bond with a amino group, e.g. a molecule with two or more carboxylic acid groups. A presently prefered molecule is a dicarboxylic acid.

Examples of molecules being able to fuse the antigens C-terminal to C-terminal is a molecule with two or more groups that are able to form a bond with a carboxylic acid group, e.g. a molecule with two or more amino groups. A presently preferred molecule is a diamine molecule. Examples of molecules being able to fuse the antigens C-terminal to N-terminal is a molecule with at least one group that is able to form a bond with an amino group and with at least one group that is able to form a bond with a carboxylic acid group, e.g. a molecule with both an amino group and a carboxylic acid group. Examples of such a molecule is an amino acid, e.g. an α-amino acid, a peptide and a polypeptide, such a peptide or polypeptide having e.g. from 2 to 1000 amino acid units. A presently preferred molecule is a peptide having a sequence of 1 to 20 amino acids, such as 2–10 amino acids.

Also, a linker can be introduced between the antigens being fused in order to enhance the immunogenicity of the fusion molecule. The linker could eg. 1) introduce one or more protease cleavage sites which would lead to a cleavage of the fusion molecule in the macrophage, 2) introduce a sequence leading to polymerisation of the fusion molecule, 3) incorporate a sequence facilitating transport of the fusion molecule across the cell membrane leading to MHC I presentation, or 4) induce a different folding of the protein leading to an altered folding of the fusion molecule and thereby a different processing resulting in presentation of another group of epitopes. The term "linker sequence" includes such linkers.

Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

The term "sequence identity" indicates a quantitative measure of the degree of homology between two amino acid sequences of equal length or between two nucleotide sequences of equal length. If the two sequences to be compared are not of equal length, they must be aligned to best possible fit possible with the insertion of gaps or alternatively, truncation at the ends of the protein sequences. The sequence identity can be calculated as $(N_{ref}-N_{dif})^{100}/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as non-identity of the specific residue(s), i.e. the DNA sequence AGTGTC will have a sequence identity of 75% with the DNA sequence AGTCAGTC ($N_{dif}=2$ and $N_{ref}=8$). Sequence identity can alternatively be calculated by the BLAST program e.g. the BLASTP program (Pearson W. R and D. J. Lipman (1988) PNAS USA 85:2444–2448)(www.ncbi.nlm.nih.gov/cgi-bin/BLAST). In one aspect of the invention, alignment is performed with the sequence alignment method ClustalW with default parameters as described by Thompson J., et al 1994, available at http://www2.ebi.ac.uk/clustalw/.

A preferred minimum percentage of sequence identity is at least 70%, such as at least 75%, at least 80%, such as at least 85%, at least 90%, at least 91%, at least 92%, at least 93%, at least 94%, at least 95%, at least 96%, at least 97%, at least 98%, at least 99%, such as at least 99.5%.

The immunogenic portion of a polypeptide is a part of the polypeptide, which elicits an immune response in an animal or a human being, and/or in a biological sample determined by any of the biological assays described herein. The immunogenic portion of a polypeptide may be a T-cell epitope or a B-cell epitope. Immunogenic portions can be related to one or a few relatively small parts of the polypeptide, they can be scattered throughout the polypeptide sequence or be situated in specific parts of the polypeptide. For a few polypeptides epitopes have even been demonstrated to be scattered throughout the polypeptide covering the full sequence (Ravn et al 1999).

In order to identify relevant T-cell epitopes which are recognized during an immune response, it is possible to use a "brute force" method: Since T-cell epitopes are linear, deletion mutants of the polypeptide will, if constructed systematically, reveal what regions of the polypeptide are essential in immune recognition, e.g. by subjecting these deletion mutants e.g. to the IFN-γ assay described herein. Another method utilises overlapping oligopeptides for the detection of MHC class II epitopes, preferably synthetic, having a length of e.g. 20 amino acid residues derived from the polypeptide. These peptides can be tested in biological assays (e.g. the IFN-γ assay as described herein) and some of these will give a positive response (and thereby be immunogenic) as evidence for the presence of a T cell epitope in the peptide. For the detection of MHC class I epitopes it is possible to predict peptides that will bind (Stryhn et al 1996) and hereafter produce these peptides synthetically and test them in relevant biological assays e.g. the IFN-γ assay as described herein. The peptides preferably having a length of e.g. 8 to 11 amino acid residues derived from the polypeptide. B-cell epitopes can be determined by analyzing the B cell recognition to overlapping peptides covering the polypeptide of interest as e.g. described in Harboe et al, 1998.

Although the minimum length of a T-cell epitope has been shown to be at least 6 amino acids, it is normal that such epitopes are constituted of longer stretches of amino acids. Hence, it is preferred that the polypeptide fragment of the invention has a length of at least 7 amino acid residues, such as at least 8, at least 9, at least 10, at least 12, at least 14, at least 16, at least 18, at least 20, at least 22, at least 24, such as at least 30 amino acid residues. Hence, in important embodiments of the inventive method, it is preferred that the polypeptide fragment has a length of at most 50 amino acid residues, such as at most 40, 35, 30, 25, e.g. at most 20 amino acid residues. It is expected that the peptides having a length of between 10 and 20 amino acid residues will prove to be most efficient as MHC class II epitopes and therefore especially preferred lengths of the polypeptide fragment used in the method according to the invention are 18, such as 15, 14, 13, 12 and even 11 amino acid residues. It is expected that the peptides having a length of between 7 and 12 amino acid residues will prove to be most efficient as MHC class I epitopes and therefore other preferred lengths of the polypeptide fragment used in the method according to the invention are 11, such as 10, 9, 8 and even 7 amino acid residues.

Immunogenic portions of polypeptides may be recognized by a broad part (high frequency) or by a minor part (low frequency) of the genetically heterogenic human population. In addition some immunogenic portions induce high immunological responses (dominant), whereas others induce lower, but still significant, responses (subdominant). High frequency><low frequency can be related to the immunogenic portion binding to widely distributed MHC molecules (HLA type) or even by multiple MHC molecules (Kilgus et al. 1991, Sinigaglia et al 1988).

In the context of providing candidate molecules for a new vaccine against tuberculosis, the subdominant epitopes are however as relevant as are the dominant epitopes since it has been show (Olsen et al 2000) that such epitopes can induce protection regardless of being subdominant.

A common feature of the polypeptides of the invention is their capability to induce an immunological response as illustrated in the examples. It is understood that a variant of a polypeptide of the invention produced by substitution, insertion, addition or deletion is also immunogenic as determined by at least one of the assays described herein.

An immune individual is defined as a person or an animal, which has cleared or controlled an infection with virulent mycobacteria or has received a vaccination with *M. bovis* BCG.

An immunogenic polypeptide is defined as a polypeptide that induces an immune response in a biological sample or an individual currently or previously infected with a virulent mycobacterium. The immune response may be monitored by one of the following methods:

An in vitro cellular response is determined by release of a relevant cytokine such as IFN-γ from lymphocytes withdrawn from an animal or human being currently or previously infected with virulent mycobacteria, or by detection of proliferation of these T cells, the induction being performed by the addition of the polypeptide or the immunogenic portion to a suspension comprising from $1 \times 10^5$ cells to $3 \times 10^5$ cells per well. The cells are isolated from either the blood, the spleen, the liver or the lung and the addition of the polypeptide or the immunogenic portion resulting in a concentration of not more than 20 µg per ml suspension and the stimulation being performed from two to five days. For monitoring cell proliferation the cells are pulsed with radioactive labeled Thymidine and after 16–22 hours of incubation detecting the proliferation by liquid scintillation counting, a positive response being a response more than background plus two standard derivations. The release of IFN-γ can be determined by the ELISA method, which is well known to a person skilled in the art, a positive response being a response more than background plus two standard derivations. Other cytokines than IFN-γ could be relevant when monitoring the immunological response to the polypeptide, such as IL-12, TNF-α, IL-4, IL-5, IL-10, IL-6, TGF-β. Another and more sensitive method for determining the presence of a cytokine (e.g. IFN-γ) is the ELISPOT method where the cells isolated from either the blood, the spleen, the liver or the lung are diluted to a concentration of preferably 1 to $4 \times 10^8$ cells/ml and incubated for 18–22 hrs in the presence of the polypeptide or the immunogenic portion resulting in a concentration of not more than 20 µg per ml. The cell suspensions are hereafter diluted to 1 to $2 \times 10^6$/ml and transferred to Maxisorp plates coated with anti-IFN-γ and incubated for preferably 4 to 16 hours. The IFN-γ producing cells are determined by the use of labelled secondary anti-IFN-γ antibody and a relevant substrate giving rise to spots, which can be enumerated using a dissection microscope. It is also a possibility to determine the presence of mRNA coding for the relevant cytokine by the use of the PCR technique. Usually one or more cytokines will be measured utilizing for example the PCR, ELISPOT or ELISA. It will be appreciated by a person skilled in the art that a significant increase or decrease in the amount of any of these cytokines induced by a specific polypeptide can be used in evaluation of the immunological activity of the polypeptide.

An in vitro cellular response may also be determined by the use of T cell lines derived from an immune individual or a person infected with M. tuberculosis where the T cell lines have been driven with either live mycobacteria, extracts from the bacterial cell or culture filtrate for 10 to 20 days with the addition of IL-2. The induction is performed by addition of not more than 20 µg polypeptide per ml suspension to the T cell lines containing from $1 \times 10^5$ cells to $3 \times 10^5$ cells per well and incubation being performed from two to six days. The induction of IFN-γ or release of another relevant cytokine is detected by ELISA. The stimulation of T cells can also be monitored by detecting cell proliferation using radioactively labeled Thymidine as described above. For both assays a positive response is a response more than background plus two standard derivations.

An in vivo cellular response which may be determined as a positive DTH response after intradermal injection or local application patch of at most 100 µg of the polypeptide or the immunogenic portion to an individual who is clinically or subclinically infected with a virulent Mycobacterium, a positive response having a diameter of at least 5 mm 72–96 hours after the injection or application.

An in vitro humoral response is determined by a specific antibody response in an immune or infected individual. The presence of antibodies may be determined by an ELISA technique or a Western blot where the polypeptide or the immunogenic portion is absorbed to either a nitrocellulose membrane or a polystyrene surface. The serum is preferably diluted in PBS from 1:10 to 1:100 and added to the absorbed polypeptide and the incubation being performed from 1 to 12 hours. By the use of labeled secondary antibodies the presence of specific antibodies can be determined by measuring the OD e.g. by ELISA where a positive response is a response of more than background plus two standard derivations or alternatively a visual response in a Western blot.

Another relevant parameter is measurement of the protection in animal models induced after vaccination with the polypeptide in an adjuvant or after DNA vaccination. Suitable animal models include primates, guinea pigs or mice, which are challenged with an infection of a virulent Mycobacterium. Readout for induced protection could be decrease of the bacterial load in target organs compared to non-vaccinated animals, prolonged survival times compared to non-vaccinated animals and diminished weight loss compared to non-vaccinated animals.

In general, M. tuberculosis antigens, and DNA sequences encoding such antigens, may be prepared using any one of a variety of procedures. They may be purified as native proteins from the M. tuberculosis cell or culture filtrate by procedures such as those described above. Immunogenic antigens may also be produced recombinantly using a DNA sequence encoding the antigen, which has been inserted into an expression vector and expressed in an appropriate host. Examples of host cells are E. coli. The polypeptides or immunogenic portion hereof can also be produced synthetically if having fewer than about 100 amino acids, generally fewer than 50 amino acids, and may be generated using techniques well known to those ordinarily skilled in the art, such as commercially available solid-phase techniques where amino acids are sequentially added to a growing amino acid chain.

In the construction and preparation of plasmid DNA encoding the polypeptide as defined for DNA vaccination a host strain such as E. coli can be used. Plasmid DNA can then be prepared from overnight cultures of the host strain carrying the plasmid of interest and purified using e.g. the Qiagen Giga-Plasmid column kit (Qiagen, Santa Clarita, Calif., USA) including an endotoxin removal step. It is essential that plasmid DNA used for DNA vaccination is endotoxin free.

The immunogenic polypeptides may also be produced as fusion proteins, by which methods superior characteristics of the polypeptide of the invention can be achieved. For instance, fusion partners that facilitate export of the polypeptide when produced recombinantly, fusion partners that facilitate purification of the polypeptide, and fusion partners which enhance the immunogenicity of the polypeptide fragment of the invention are all interesting possibilities. Therefore, the invention also pertains to a fusion polypeptide comprising at least one polypeptide or immunogenic portion defined above and at least one fusion partner. The fusion partner can, in order to enhance immunogenicity, be another polypeptide derived from M. tuberculosis, such as of a polypeptide fragment derived from a bacterium belonging to the tuberculosis complex, such as TB10.4, CFP10, RD1-

ORF5, RD1-ORF2, Rv1036, MPB64, MPT64, Ag85A, MPB59, Ag85C, 19 kDa lipoprotein, MPT32 and alpha-crystallin, or at least one T-cell epitope of any of the above mentioned antigens ((Skjøt et al, 2000; Danish Patent application PA 2000 00666; Danish Patent application PA 1999 01020; U.S. patent application Ser. No. 09/0505,739; Rosenkrands et al, 1998; Nagai et al, 1991).

Other fusion partners, which could enhance the immunogenicity of the product, are lymphokines such as IFN-γ, IL-2 and IL-12. In order to facilitate expression and/or purification, the fusion partner can e.g. be a bacterial fimbrial protein, e.g. the pilus components pilin and papA; protein A; the ZZ-peptide (ZZ-fusions are marketed by Pharmacia in Sweden); the maltose binding protein; gluthatione S-transferase; β-galactosidase; or poly-histidine. Fusion proteins can be produced recombinantly in a host cell, which could be *E. coli,* and it is a possibility to induce a linker region between the different fusion partners.

Other interesting fusion partners are polypeptides, which are lipidated so that the immunogenic polypeptide is presented in a suitable manner to the immune system. This effect is e.g. known from vaccines based on the Borrelia burgdorferi OspA polypeptide as described in e.g. WO 96/40718 A or vaccines based on the Pseudomonas aeruginosa Oprl lipoprotein (Cote-Sierra J, et al, 1998). Another possibility is N-terminal fusion of a known signal sequence and an N-terminal cystein to the immunogenic polypeptide. Such a fusion results in lipidation of the immunogenic polypeptide at the N-terminal cystein, when produced in a suitable production host.

Another part of the invention pertains to a vaccine composition comprising a polypeptide according to the invention. In order to ensure optimum performance of such a vaccine composition it is preferred that it comprises an immunologically and pharmaceutically acceptable carrier, vehicle or adjuvant.

An effective vaccine, wherein a polypeptide of the invention is recognized by the animal, will in an animal model be able to decrease bacterial load in target organs, prolong survival times and/or diminish weight loss after challenge with a virulent Mycobacterium, compared to non-vaccinated animals.

Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of dimethyidioctadecylammonium bromide (DDA), Quil A, poly I:C, aluminium hydroxide, Freund's incomplete adjuvant, IFN-γ, IL-2, IL-12, monophosphoryl lipid A (MPL), Treholose Dimycolate (TDM), Trehalose Dibehenate and muramyl dipeptide (MDP).

Preparation of vaccines which contain peptide sequences as active ingredients is generally well understood in the art, as exemplified by U.S. Pat. Nos. 4,608,251; 4,601,903; 4,599,231 and 4,599,230, all incorporated herein by reference.

Other methods of achieving adjuvant effect for the vaccine include use of agents such as aluminum hydroxide or phosphate (alum), synthetic polymers of sugars (Carbopol), aggregation of the protein in the vaccine by heat treatment, aggregation by reactivating with pepsin treated (Fab) antibodies to albumin, mixture with bacterial cells such as C. parvum or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Other possibilities involve the use of immune modulating substances such as cytokines or synthetic IFN-γ inducers such as poly I:C in combination with the above-mentioned adjuvants.

Another interesting possibility for achieving adjuvant effect is to employ the technique described in Gosselin et al., 1992 (which is hereby incorporated by reference herein). In brief, a relevant antigen such as an antigen of the present invention can be conjugated to an antibody (or antigen binding antibody fragment) against the Fcγ receptors on monocytes/macrophages.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 μg to 1000 μg, such as in the range from about 1 μg to 300 μg, and especially in the range from about 10 μg to 50 μg. Suitable regimens for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10–95% of active ingredient, preferably 25–70%.

In many instances, it will be necessary to have multiple administrations of the vaccine. Especially, vaccines can be administered to prevent an infection with virulent mycobacteria and/or to treat established mycobacterial infection. When administered to prevent an infection, the vaccine is given prophylactically, before definitive clinical signs or symptoms of an infection are present.

Due to genetic variation, different individuals may react with immune responses of varying strength to the same polypeptide. Therefore, the vaccine according to the invention may comprise several different polypeptides in order to increase the immune response. The vaccine may comprise two or more polypeptides or immunogenic portions, where all of the polypeptides are as defined above, or some but not all of the peptides may be derived from virulent mycobacteria. In the latter example, the polypeptides not necessarily fulfilling the criteria set forth above for polypeptides may either act due to their own immunogenicity or merely act as adjuvants.

The vaccine may comprise 1–20, such as 2–20 or even 3–20 different polypeptides or fusion polypeptides, such as 3–10 different polypeptides or fusion polypeptides.

The invention also pertains to a method for immunizing an animal, including a human being, against TB caused by virulent mycobacteria, comprising administering to the animal the polypeptide of the invention, or a vaccine composition of the invention as described above, or a living vaccine described above.

The invention also pertains to a method for producing an immunologic composition according to the invention, the method comprising preparing, synthesizig or isolating a polypeptide according to the invention, and solubilizing or dispersing the polypeptide in a medium for a vaccine, and optionally adding other *M tuberculosis* antigens and/or a carrier, vehicle and/or adjuvant substance.

The nucleic acid fragments of the invention may be used for effecting in vivo expression of antigens, ie. the nucleic acid fragments may be used in so-called DNA vaccines as reviewed in Ulmer et al., 1993, which is included by reference.

Hence, the invention also relates to a vaccine comprising a nucleic acid fragment according to the invention, the vaccine effecting in vivo expression of antigen by an animal, including a human being, to whom the vaccine has been administered, the amount of expressed antigen being effective to confer substantially increased resistance to infections caused by virulent mycobacteria in an animal, including a human being.

The efficacy of such a DNA vaccine can possibly be enhanced by administering the gene encoding the expression product together with a DNA fragment encoding a polypeptide which has the capability of modulating an immune response.

One possibility for effectively activating a cellular immune response for a vaccine can be achieved by expressing the relevant antigen in a vaccine in a non-pathogenic microorganism or virus. Well-known examples of such microorganisms are *Mycobacterium bovis* BCG, *Salmonella* and *Pseudomona* and examples of viruses are Vaccinia Virus and Adenovirus.

Therefore, another important aspect of the present invention is an improvement of the living BCG (Bacillus Calmette-Guerin) vaccine presently available, wherein one or more copies of a DNA sequence encoding one or more polypeptide as defined above has been incorporated into the genome of the micro-organism in a manner allowing the micro-organism to express and secrete the polypeptide. The incorporation of more than one copy of a nucleotide sequence of the invention is contemplated to enhance the immune response Another possibility is to integrate the DNA encoding the polypeptide according to the invention in an attenuated virus such as the vaccinia virus or Adenovirus (Rolph et al 1997). The recombinant vaccinia virus is able to replicate within the cytoplasma of the infected host cell and the polypeptide of interest can therefore induce an immune response, which is envisioned to induce protection against TB.

The invention also relates to the use of a polypeptide or nucleic acid of the invention for use as a therapeutic vaccine which concept has been described in the literature exemplified by D. Lowry (1999, Nature 400: 269–71). Antigens with therapeutic properties may be identified based on their ability to diminish the severity of *M. tuberculosis* infection in experimental animals or prevent reactivation of previous infection, when administered as a vaccine. The composition used for therapeutic vaccines can be prepared as described above for vaccines.

Concordance list

| | Synonyms | DNA SEQ ID NO | Protein SEQ ID NO |
|---|---|---|---|
| ESAT-6 | | | 1 |
| Ag85B | MTP59 | | 2 |
| Ag85B-ESAT6 hybrid | MPT59-ESAT6 hybrid | | 3 |
| ESAT6-Ag85B hybrid | ESAT6-MPT59 hybrid | | 4 |
| OPBR-4 | | 5 | |
| OPBR-28 | | 6 | |
| OPBR-48 | | 7 | |
| OPBR-3 | | 8 | |
| OPBR-75 | | 9 | |
| OPBR-76 | | 10 | |
| OPBR-77 | | 11 | |
| OPBR-18 | | 12 | |

LEGENDS TO FIGURES

FIG. 1. SDS-PAGE analysis of purified recombinant *M. tuberculosis* antigens. 1 μg of protein was loaded in each lane. Lane 1: molecular weight standard; Lane 2: recombinant ESAT-6; Lane 3: recombinant Ag85B; Lane 4: Ag85B-ESAT-6 fusion protein. Lane 5: ESAT-6-Ag85B fusion protein. Protein bands were visualized by Coomassie staining.

FIG. 2. Antigen-specific responses by blood lymphocytes one week after the last immunization with the fusion proteins between Ag85B and ESAT-6. C57BL/6J mice were immunized three times with either Ag85B-ESAT-6 (Panel A) or ESAT-6-Ag85B (Panel B) emulsified in MPL-DDA. As a negative control a group of mice received the adjuvant combination alone (Panel C). The IFN-γ responses were measured in cell cultures pooled from 8 animals in each group. Each point represents the mean of triplicate values ±SEM. The experiment was performed twice with similar results.

Figure 3:
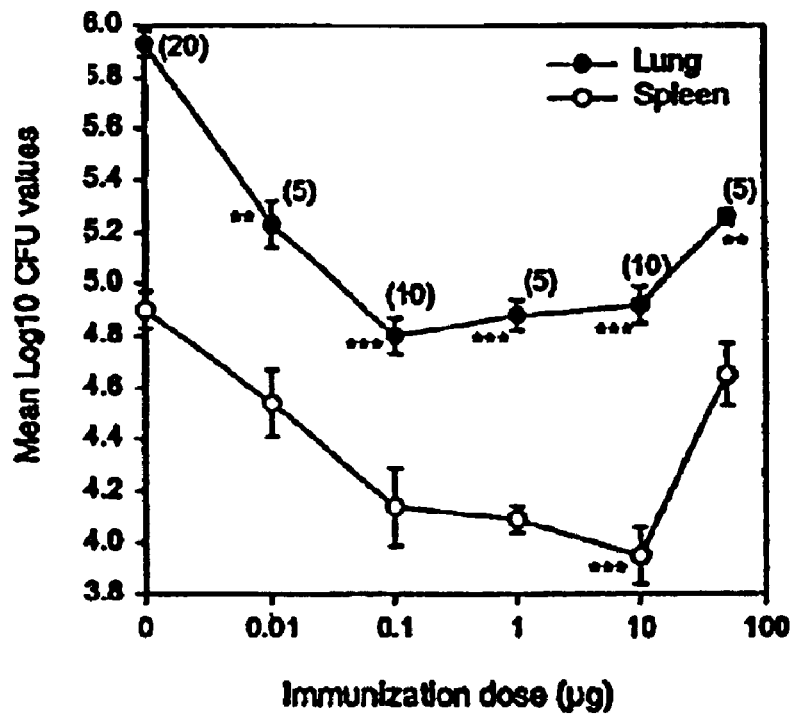

FIG. 3. Efficacy of different doses of a subunit vaccine based on Ag85B-ESAT-6. C57BI/6J mice were immunized s.c. three times with different doses of Ag85B-ESAT-6 emulsified in MPL-DDA. Mice immunized with the adjuvant alone were included. Ten weeks after the first vaccination, the mice received an aerosol challenge with *M. tuberculosis* Erdman and the numbers of bacteria (CFU's) were quantified in the lungs and spleens 6 weeks later. The values are shown as $\log_{10}$ CFU's in the lung and spleen. All data represent the mean of five to twenty individual mice ±SEM. The number in bracket indicates the number of animals in each group. The CFU's found in naive mice were 5.74±0.04 and 4.65±0.22 (n=10) in the lung and spleen, respectively. P<0.01, *P<0.001 when compared to naive mice.

Figure 4:
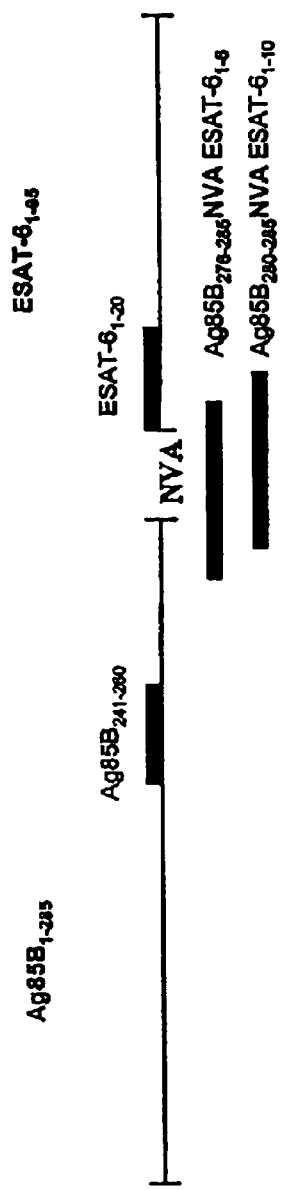

FIG. 4. Schematic representation of the fusion protein of Ag85B and ESAT-6. Synthetic peptides representing previously identified mouse T cell epitopes ($Ag85B_{241-260}$ and $ESAT-6_{1-20}$) and potential epitopes in the linker region between the two molecules ($Ag85B_{276-285}NVAESAT-6_{1-6}$ and $Ag85B_{280-285}NVAESAT-6_{1-10}$) are indicated.

Figure 5:
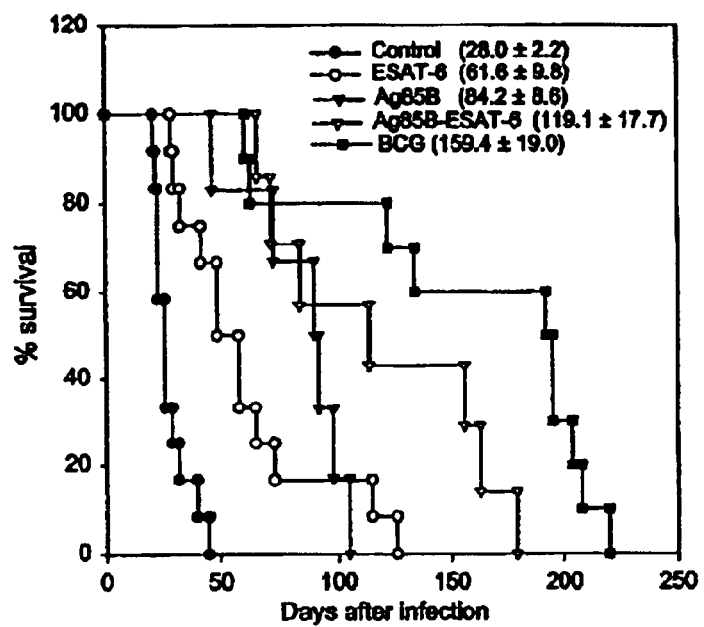

FIG. 5. Dynamics of mortality in *M. tuberculosis*-infected mice. Groups of 6–12 mice were vaccinated s.c. with either protein-based vaccines or live BCG as described in the example and challenged with a standard lethal dose of $5 \times 10^5$ *M. tuberculosis* H37Rv CFUs. Numbers in parentheses indicate the mean survival time (MST±SEM) in days.

Figure 6:
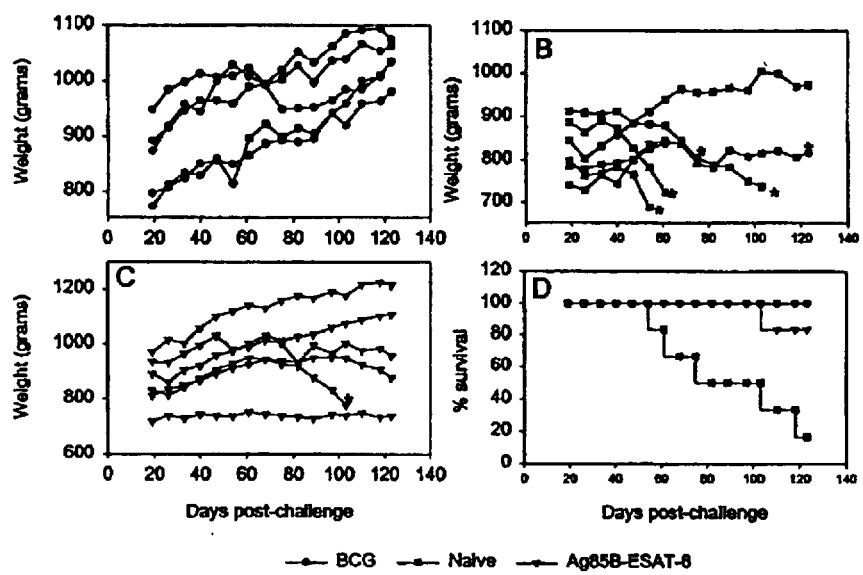

FIG. 6. Body weights of guinea pigs aerosol-infected with *M. tuberculosis*. The guinea pigs were either vaccinated with BCG, Ag85B-ESAT-6, or adjuvant-control (n=6). Data are depicted in grams. *, euthanized because of 20% weight loss or severe illness.

Figure 7:
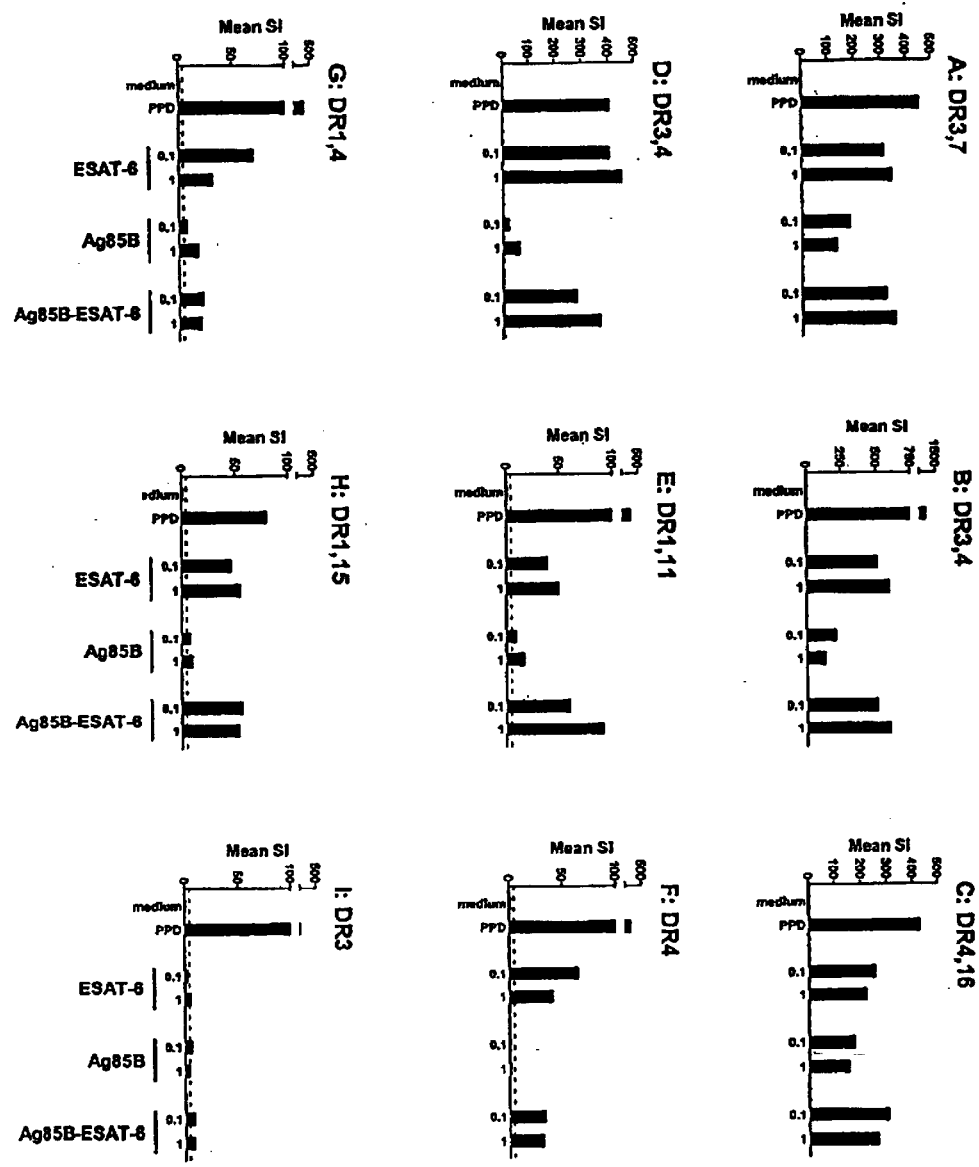

FIG. 7. Proliferation of *M. tuberculosis*-specific human T cell lines (A-I) with different HLA-DR types in response to ESAT-6, Ag85B and the fusion proteins. Data are expressed as stimulation indices (SI, calculated as mean CPM in the presence of antigen divided by the mean CPM without antigen). Dotted lines indicate SI=5. Antigen concentrations are in µg/ml.

Figure 8:
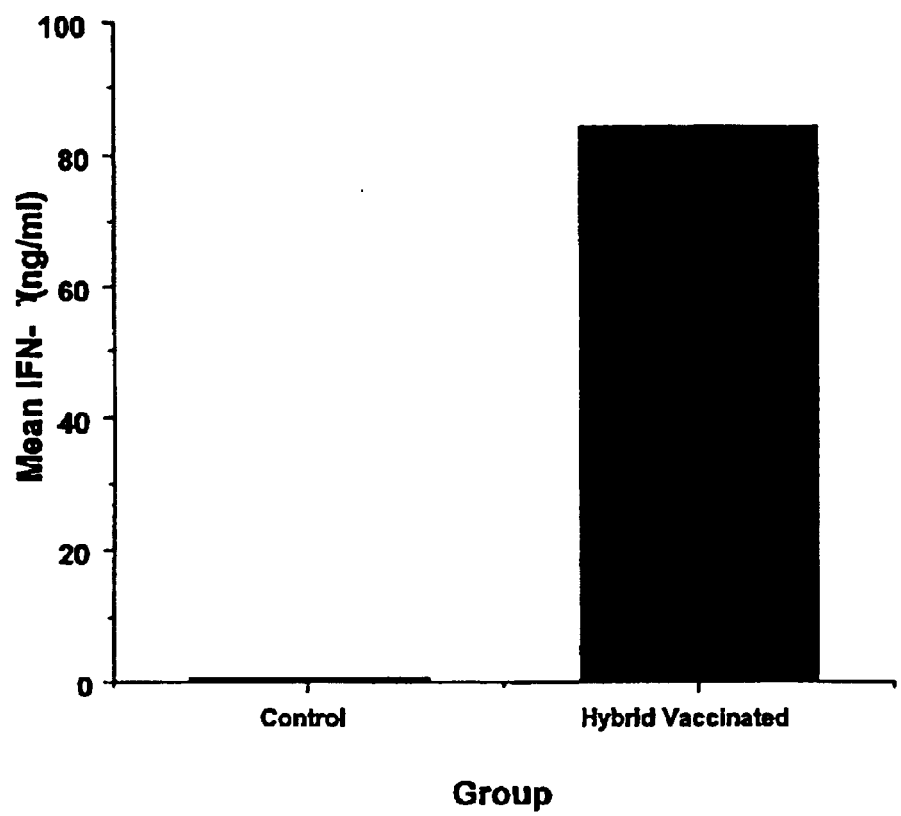

FIG. 8. IFN-γ production, one week post vaccination, in cultures of PBMC from vaccinated or control cynomolgous monkeys (n=3) after 4 days restimulation with the hybrid 1 antigen in vitro.

Figure 9:
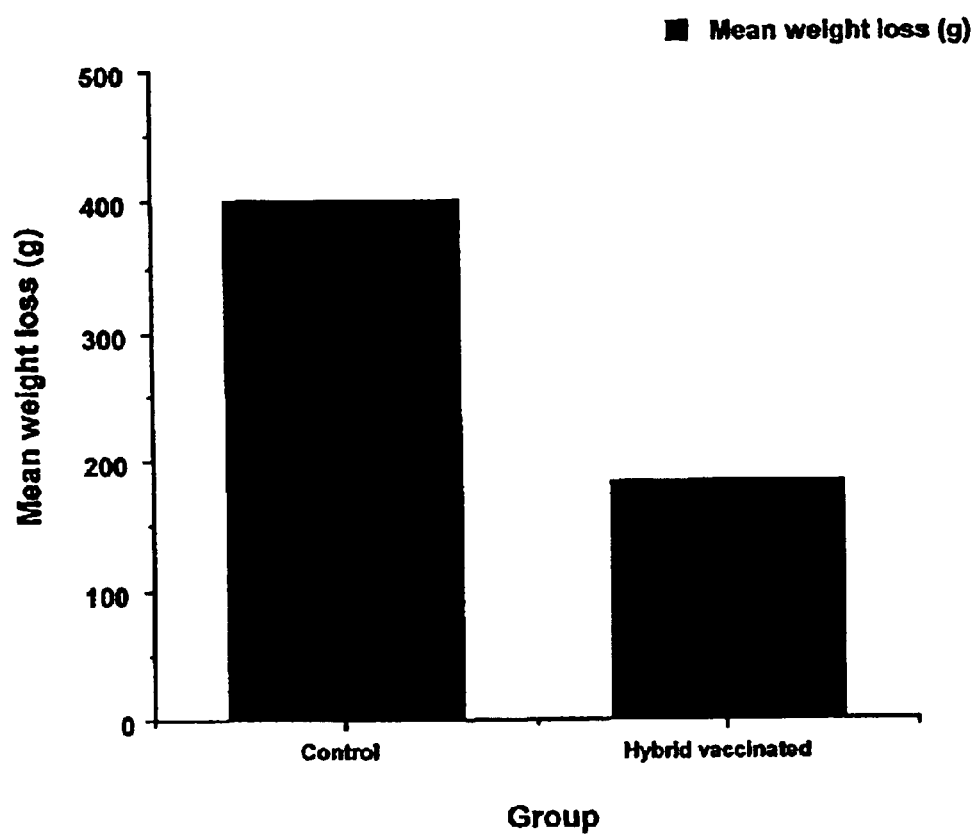

FIG. 9. Mean weight loss in vaccinated and unvaccinated cynomolgous monkeys 12 weeks after intratracheal infection with *M. tuberculosis*.

Figure 10:
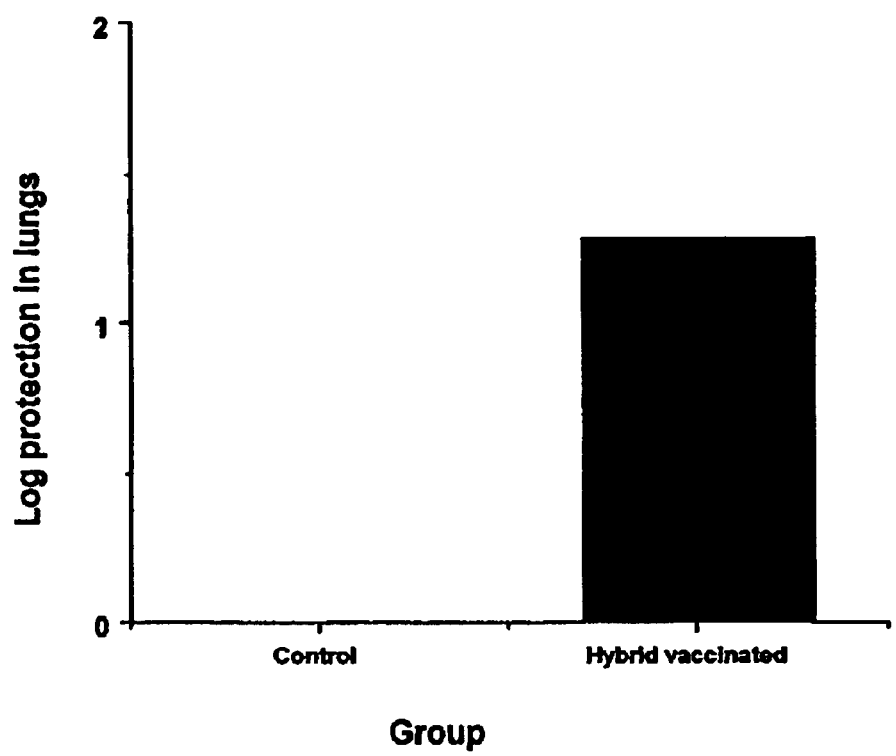

FIG. 10. Vaccine efficacy in vaccinated cynomolgous monkeys (n=3) compared to unvaccinated controls, 12 weeks after intratracheal infection with *M. tuberculosis*. Protection is expressed as the log of the mean difference between the number of bacteria detected in the lungs of vaccinated and unvaccinated animals.

EXAMPLE 1

Cloning of the ESAT6-Ag85B and the Ag85B-ESAT6 Hybrids

Background for ESAT-Aq85B and Aq85B-ESAT6 Fusion

Several studies have demonstrated that ESAT-6 is an immunogen which is relatively difficult to adjuvate in order to obtain consistent results when immunizing therewith. To detect an in vitro recognition of ESAT-6 after immunization with the antigen is very difficult compared to the strong recognition of the antigen that has been found during the recall of memory immunity to *M. tuberculosis*. ESAT-6 has been found in ST-CF in a truncated version were amino acids 1–15 have been deleted. The deletion includes the main T-cell epitopes recognized by C57BL/6j mice (Brandt et al., 1996). This result indicates that ESAT-6 either is N-terminally processed or pro-teolytically degraded in STCF. In order to optimize ESAT-6 as an immunogen, a gene fusion between ESAT-6 and another major T cell antigen Ag85B has been constructed. Two different construct have been made: Ag85B-ESAT-6 (SEQ ID NO: 3) and ESAT-6-Ag85B (SEQ ID NO: 4). In the first hybrid ESAT-6 is N-terminally protected by Ag85B and in the latter it is expected that the fusion of two dominant T-cell antigens can have a synergistic effect.

The genes encoding the ESAT6-Ag85B and the Ag85B-ESAT6 hybrids were cloned into the expression vector pMCT6, by PCR amplification with gene specific primers, for recombinant ex-pression in *E. coli* of the hybrid proteins.

Construction of the Hybrid Aq85B-ESAT6

The cloning was carried out in three steps. First the genes encoding the two components of the hybrid, ESAT6 and Ag85B, were PCR amplified using the following primer constructions:

ESAT6

```
OPBR-4:  GGCGCCGGCAAGCTTGCCATGACAGAGCAGCAGTGG (SEQ
                                                ID
                                                NO: 5)

OPBR-28:CGAACTCGCCGGATCCCGTGTTTCGC            (SEQ
                                                ID
                                                NO: 6)
```

OPBR-4 and OPBR-28 create HinDIII and BamHI sites, respectively.

```
OPBR-48:GGCAACCGCGAGATCTTTCTCCCGGCCGGGGC  (SEQ ID
                                           NO: 7)

OPBR-3:  GGCAAGCTTGCCGGCGCCTAACGAACT       (SEQ ID
                                           NO: 8)
```

OPBR-48 and OPBR-3 create BglII and HinDIII, respectively. Additionally OPBR-3 deletes the stop codon of Ag85B.

PCR reactions contained 10 ng of *M. tuberculosis* chromosomal DNA in 1×low salt Taq+ buffer from Stratagene supplemented with 250 mM of each of the four nucleotides (Boehringer Mann-heim), 0,5 mg/ml BSA (IgG technology), 1% DMSO (Merck), 5 pmoles of each primer and 0.5 unit Tag+DNA polymerase (Stratagene) in 10 μl reaction volume. Reactions were initially heated to 94° C. for 25 sec. and run for 30 cycles of the program; 94° C. for 10 sec., 55° C. for 10 sec. and 72° C. for 90 sec, using thermocycler equipment from Idaho Technology.

The DNA fragments were subsequently run on 1% agarose gels, the bands were excised and purified by Spin-X spin columns (Costar). The two PCR fragments were digested with HinDIll and ligated. A PCR amplification of the ligated PCR fragments encoding Ag85B-ESAT6 was carried out using the primers OPBR-48 and OPBR-28. PCR reaction was initially heated to 94° C. for 25 sec. and run for 30 cycles of the program; 94° C. for 30 sec., 55° C. for 30 sec. and 72° C. for 90 sec. The resulting PCR fragment was digested with BgIII and BamHI and cloned into the expression vector pMCT6 in frame with 8 histidines, which are added to the N-terminal of the expressed protein hybrid. The resulting clones were hereafter sequenced by use of the dideoxy chain termination method adapted for supercoiled DNA using the Sequenase DNA sequencing kit version 1.0 (United States Biochemical Corp., USA) and by cycle sequencing using the Dye Terminator system in combination with an automated gel reader (model 373A; Applied Biosystems) according to the instructions provided. Both strands of the DNA were sequenced.

Construction of the Hybrid ESAT6-Aq85B

Construction of the hybrid ESAT6-Ag85B was carried out as described for the hybrid Ag85B-ESAT6. The primers used for the construction and cloning were:

ESAT6

OPBR-75: GGACCCAGATCTATGACAGAGCAGCAGTGG (SEQ ID NO: 9)

OPBR-76: CCGGCAGCCCCGGCCGGGAGAAAAGCTTTGCGAACATCCCAGTGACG (SEQ ID NO: 10)

OPBR-75 and OPBR-76 create BgIII and HinDII sites, respectively. Additionally OPBR-76 deletes the stop codon of ESAT6.

Ag85B

OPBR-77: GTTCGCAAAGCTTTTCTCCCGGCCGGGGCTGCCGGTCGAGTACC (SEQ ID NO: 11)

OPBR-18: CCTTCGGTGGATCCCGTCAG (SEQ ID NO: 12)

OPBR-77 and OPBR-18 create HinDIII and BamHI sites, respectively.

Expression/purification of Aq85B-ESAT6 and ESAT6-Aq85B Hybrid Proteins Expression and metal affinity purification of recombinant proteins was undertaken essentially as described by the manufacturers. For each protein, 1 ILB-media containing 100 µg/ml ampicillin, was inoculated with 10 ml of an overnight culture of XL1-Blue cells harbouring recombinant pMCT6 plasmids. Cultures were shaken at 37° C. until they reached a density of $OD_{600}$= 0.4–0.6. IPTG was hereafter added to a final concentration of 1 mM and the cultures were further incubated 4–16 hours. Cells were harvested, resuspended in 1×sonication buffer+8 M urea and sonicated 5×30 sec. with 30 sec. pausing between the pulses.

After centrifugation, the lysate was applied to a column containing 25 ml of resuspended Talon resin (Clontech, Palo Alto, USA). The column was washed and eluted as described by the manufacturers.

After elution, all fractions (1.5 ml each) were subjected to analysis by SDS-PAGE using the Mighty Small (Hoefer Scientific Instruments, USA) system and the protein concentrations were estimated at 280 nm. Fractions containing recombinant protein were pooled and dialysed against 3 M urea in 10 mM Tris-HCI, pH 8.5. The dialysed protein was further purified by FPLC (Pharmacia, Sweden) using a 6 ml Resource-Q column, eluted with a linear 0–1 M gradient of NaCl. Fractions were analyzed by SDS-PAGE and protein concentrations were estimated at $OD_{280}$. Fractions containing protein were pooled and dialysed against 25 mM Hepes buffer, pH 8.5.

Finally the protein concentration and the LPS content were determined by the BCA (Pierce, Holland) and LAL (Endosafe, Charleston, USA) tests, respectively.

EXAMPLE 2

Biological Activity of the Purified Antigens

IFN-γ Induction in the Mouse Model of TB Infection

The recognition of the purified antigens in the mouse model of memory immunity to TB was investigated.

A group of efficiently protected mice was generated by infecting 8–12 weeks old female C57Bl/6j mice with $5×10^4$ M. tuberculosis i.v. After 30 days of infection the mice were subjected to 60 days of antibiotic treatment with isoniazid and were then left for 200–240 days to ensure the establishment of resting long-term memory immunity. Such memory immune mice are very efficiently protected against a secondary infection. Long lasting immunity in this model is mediated by a population of highly reactive CD4 cells recruited to the site of infection and triggered to produce large amounts of IFN-γ in response to ST-CF (Andersen et al. 1995).

We have used this model to identify single antigens recognized by protective T cells. Memory immune mice were reinfected with $1×10^6$ M. tuberculosis i.v. and splenic lymphocytes were harvested at day 4–6 of reinfection, a time point where this population is highly reactive to ST-CF.

Skin Test Reaction in TB Infected Guinea Pigs

The skin test activity of the purified proteins was tested in M. tuberculosis infected guinea pigs.

1 group of guinea pigs was infected via an ear vein with $1×10^4$ CFU of M. tuberculosis H37Rv in 0,2 ml PBS. After 4 weeks skin tests were performed and 24 hours after injection erythema diameter was measured.

Together these analyses indicate that most of the antigens identified were highly biologically active and recognized during TB infection in different animal models.

TABLE 1

DTH erythema diameter in guinea pigs i.v. infected with $1 × 10^4$ CFU M. tuberculosis, after stimulation with 10 µg antigen.

| Antigen | Mean (mm) | SEM |
|---|---|---|
| PBS | 3.25 | 0.48 |
| PPD (2TU) | 10.88 | 1 |
| Ag85B-ESAT6 | 14.75 | 1.5 |

The values presented are the mean of erythema diameter of four animals.

The results in Table 1 indicates biological activity of Ag85B-ESAT-6 resulting in a DTH response at the level of PPD.

Biological Activity of the Purified Recombinant Antigens
Interferon-γ Induction in the Mouse Model of TB Infection Primary infections. 8 to 12 weeks old female C57BL/6j (H-$2^b$), CBA/J(H-$2^k$), DBA.2(H-$2^d$) and A.SW(H-$2^s$) mice (Bomholtegaard, Ry) were given intravenous infections via the lateral tail vein with an inoculum of 5×10$^4$ *M. tuberculosis* suspended in PBS in a vol. of 0.1 ml. 14 days postinfection the animals were sacrificed and spleen cells were isolated and tested for the recognition of recombinant antigen.

As shown in TABLE 2, the recombinant antigen Ag85B-ESAT6 was recognized in all four strains of mice at a level comparable to ST-CF, whereas ESAT6-Ag85B only was recognized in one strain at this level.

Memory responses. 8–12 weeks old female C57BL/6j(H-$2^b$) mice (Bomholtegaard, Ry) were given intravenous infections via the lateral tail vein with an inoculum of 5×10$^4$ *M. tuberculosis* suspended in PBS in a vol. of 0.1 ml. After 1 month of infection the mice were treated with isoniazid (Merck and Co., Rahway, N.J.) and rifabutin (Farmatalia Carlo Erba, Milano, Italy) in the drinking water, for two months. The mice were rested for 4–6 months before being used in experiments. For the study of the recall of memory immunity, animals were infected with an inoculum of 1×10$^6$ bacteria i.v. and sacrificed at day 4 postinfection. Spleen cells were isolated and tested for the recognition of recombinant antigen.

As shown in TABLE 3, IFN-γ release after stimulation with Ag85B-ESAT6 and ESAT6-Ag85B was at the same level as seen from spleen cells stimulated with ST-CF.

TABLE 2

T cell responses in primary TB infection.

| Name | C57Bl/6j (H2$^b$) | DBA.2 (H2$^d$) | CBA/J (H2$^k$) | A.SW (H2$^s$) |
|---|---|---|---|---|
| Ag85B-ESAT6 | +++ | +++ | +++ | ++ |
| ESAT6-Ag85B | +++ | − | + | − |

Mouse IFN-γ release 14 days after primary infection with *M. tuberculosis*.
−: no response; +: 1/3 of ST-CF; ++: 2/3 of ST-CF; +++: level of ST-CF.
n.d. = not determined.

TABLE 3

T cell responses in memory immune animals.

| Name | Memory response |
|---|---|
| Ag85B-ESAT6 | +++ |
| ESAT6-Ag85B | +++ |

Mouse IFN-γ release during recall of memory immunity to *M. tuberculosis*.
−: no response; +: 1/3 of ST-CF; ++: 2/3 of ST-CF; +++: level of ST-CF.

Interferon-γ Induction in Human TB Patients and BCG Vaccinated People

Human donors: PBMC were obtained from healthy BCG vaccinated donors with no known exposure to patients with TB and from patients with culture or microscopy proven infection with *Mycobacterium tuberculosis*. Blood samples were drawn from the TB patients 1–4 months after diagnosis.

Cytokine analysis: Interferon-γ (IFN-γ) was measured with a standard ELISA technique using a commercially available pair of mAb's from Endogen and used according to the instructions for use. Recombinant IFN-γ (Gibco laboratories) was used as a standard. The detection level for the assay was 50 pg/ml. The variation between the duplicate wells did not exceed 10% of the mean. As seen from Table 9B Ag85B-ESAT6 and ESAT6-Ag85B both give rise to IFN-γ responses at the level of ST-CF and 67–89% show high responses (>1000 pg/ml).

TABLE 4

Results from the stimulation of human blood cells from 9 Healthy BCG vaccinated, or non vaccinated ST-CF positive and 8 Tb patients with recombinant Ag85B-ESAT6 and ESAT6-Ag85B are shown. ST-CF, PPD and PHA are included for comparison. Results are given in pg IFN-γ/ml and negative values below 300 pg/ml are shown as "<". nd = not done.

| Donor | no ag | PHA | PPD | STCF | Ag85B-ESAT6 | ESAT6-Ag85B |
|---|---|---|---|---|---|---|
| Controls, Healthy BCG vaccinated, or non vaccinated ST-CF positive. | | | | | | |
| 1 | < | 9560 | 6770 | 3970 | 2030 | < |
| 2 | < | 12490 | 6600 | 8070 | 5660 | 5800 |
| 4 | < | 21030 | 4100 | 3540 | < | < |
| 5 | < | 18750 | 14200 | 13030 | 8540 | < |
| 11 | < | nd | 5890 | 4040 | 4930 | 8870 |
| 12 | < | nd | 6470 | 3330 | 2070 | 6450 |
| 14 | < | 8310 | nd | 2990 | 10270 | 11030 |
| 15 | < | 10830 | nd | 4160 | 3880 | 4540 |
| 16 | < | 8710 | nd | 5690 | 2240 | 5820 |
| Tb patients, 1–4 month after diagnosis | | | | | | |
| 6 | < | 8970 | 5100 | 6150 | 4150 | 4120 |
| 7 | < | 12410 | 6280 | 3390 | 5050 | 2040 |
| 8 | < | 11920 | 7670 | 7370 | 800 | 1350 |
| 9 | < | 22130 | 16420 | 17210 | 13660 | 5630 |
| 23 | < | 10070 | nd | 3730 | 1740 | 2390 |
| 24 | < | 10820 | nd | 6180 | 1270 | 1570 |
| 25 | < | 9010 | nd | 3200 | 3680 | 5340 |
| 26 | < | 10740 | nd | 7650 | 2070 | 620 |

EXAMPLE 3

Four groups of 6–8 weeks old, female C57Bl/6J mice (Bomholtegård, Denmark) were immunized subcutaneously at the base of the tail with vaccines of the following compositions:

Group 1: 10 μg ESAT-6/DDA (250 μg)
Group 2: 10 μg Ag85B/DDA (250 μg)
Group 3: 10 μg Ag85B-ESAT-6 /DDA (250 μg)
Group 4: Adjuvant control group: DDA (250 μg) in NaCl The animals were injected with a volume of 0.2 ml. Two weeks after the first injection and 3 weeks after the second injection the mice were boosted a little further up the back. One week after the last immunization the mice were bled and the blood cells were isolated. The immune response induced was monitored by release of IFN-γ into the culture supernatants when stimulated in vitro with relevant antigens (see the following table).

| Immunogen | For restimulation[a)]: Ag in vitro | | | |
|---|---|---|---|---|
| 10 μg/dose | no antigen | ST-CF | ESAT-6 | Ag85B |
| ESAT-6 | 219 ± 219 | 569 ± 569 | 835 ± 633 | — |
| Ag85B | 0 | 802 ± 182 | — | 5647 ± 159 |

-continued

| Immunogen | For restimulation[a]: Ag in vitro | | | |
|---|---|---|---|---|
| 10 µg/dose | no antigen | ST-CF | ESAT-6 | Ag85B |
| Hybrid: Ag85B-ESAT-6 | 127 ± 127 | 7453 ± 581 | 15133 ± 861 | 16363 ± 1002 |

Figure 2:
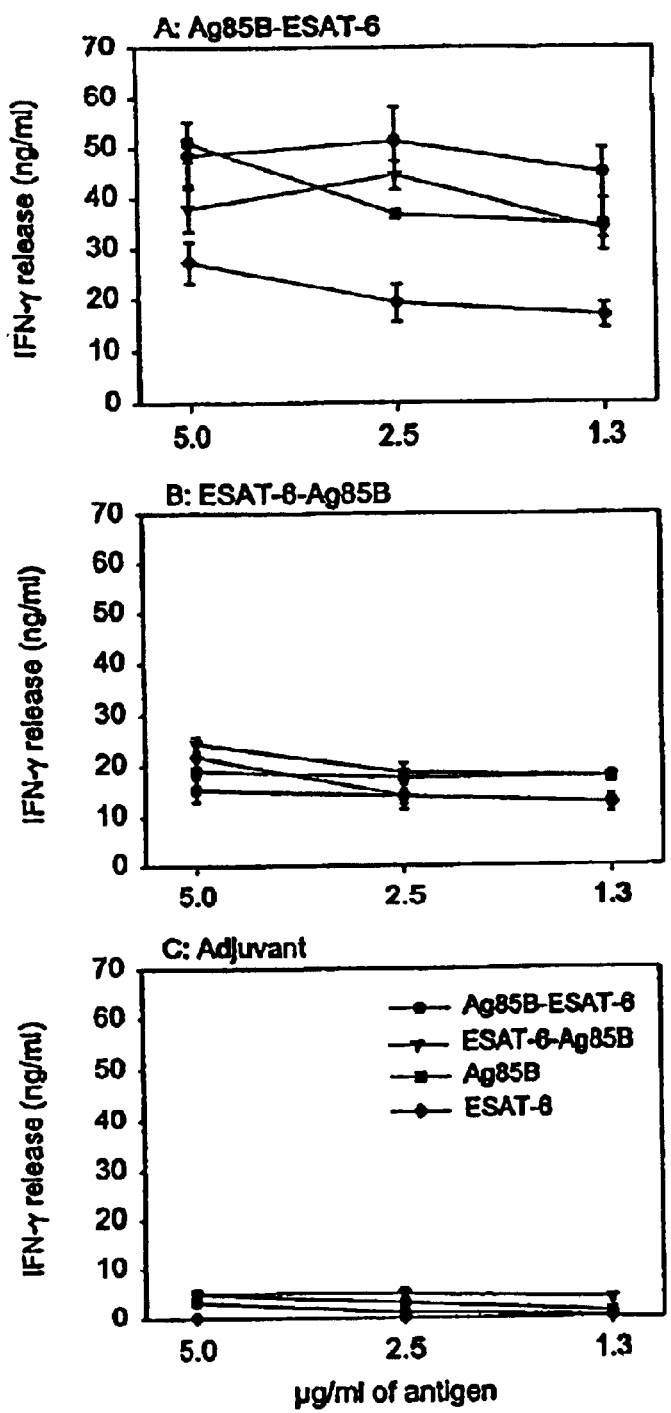

[a]Blood cells were isolated 1 week after the last immunization and the release of IFN-γ (pg/ml) after 72 h of antigen stimulation (5 µg/ml) was measured. The values shown are mean of triplicates performed on cells pooled from three mice ± SEM
[b]— not determined The experiment demonstrates that immunization with the hybrid stimulates T cells which recognize ESAT-6 and Ag85B stronger than after single antigen immunization. Especially the recognition of ESAT-6 was enhanced by immunization with the Ag85B-ESAT-6 hybrid. IFN-γ release in control mice immunized with DDA never exceeded 1000 pg/ml.

EXAMPLE 4

Experimental Vaccines Based on Recombinant Fusion Proteins Between Ag85B and ESAT-6

Animals

Specific-pathogen-free female C57BL/6J (H-2b) and B6CBAF1 (H-2b,k) mice were purchased from Bomholtgaard (Ry, Denmark). All mice used were 6–12 wk of age and were housed in cages contained within a BL-3 laminar flow safety enclosure. Animals were allowed free access to water and standard mouse chow.

Bacteria

*M. tuberculosis* Erdman and H37Rv was grown at 37° C. in modified Sauton medium enriched with 0.5% sodium pyruvate and 0.5% glucose. BCG Danish 1331 was obtained as a freeze dried vaccine and was rehydrated with PBS.

Mycobacterial Antigens

Recombinant Ag85B was produced as follows:

The coding region of ag85B was amplified by PCR from *M. tuberculosis* H37Rv chromosomal DNA with the following primer sets:

```
OPBR-77: GTTCGCAAAGCTTTTCTCCCGGCCGGGGCTGCCGGTCGAGTACC (SEQ ID NO: 11)
                HindIII OPBR-18: CCTTCGGTGGATCCCGTCAG                          (SEQ ID NO: 12)
               BamHI
```

For the production of recombinant Ag85B, the coding region (without the secretory signal sequence) of Ag85B was PCR amplified from *M. tuberculosis* H37Rv chromosomal DNA using Ag85B-F1 and Ag85B-R2 primers. A unique BamHI site was introduced by the Ag85B-R2 primer. The PCR product was digested by BglII and BamHI and cloned into pMCT6 (Harboe et al. 1998). DNA sequences of the inserts were confirmed by sequencing. The His-tagged protein was expressed in *E. coli* XL-1 blue and purified on a TALON column followed by protein anion-exchange chromatography using a HiTrap® Q column (Pharmacia, Uppsala, Sweden). The sample was dialyzed against 25 mM HEPES buffer (pH 8.0), 0.15 M NaCl, 10% glycerol and 0.01% Tween 20, and stored at −20° C.

Vaccine Preparation and Immunization Procedure

Mice were immunized with experimental vaccines in doses from 0.01–50 μg emulsified with 250 μg dimethyl dioctadecylammonium bromide (DDA) (Eastman Kodak, Rochester, N.Y.) co-adjuvanted with 25 μg monophosphoryl Lipid A (MPL) (RIBI; Immunochem. Research Inc., Montana, USA). The vaccines (0.2 ml/mice) were injected three times subcutaneously (s.c.) on the back with two weeks interval. A single dose of BCG Danish 1331 (5×104 bacilli/mouse) was injected s.c. at the base of the tail at the same time as the first subunit vaccination, no booster injections were administered. The pre-challenge immunity was evaluated with blood lymphocytes five weeks after the first vaccination.

Lymphocyte Cultures

Blood lymphocytes were purified on a density gradient. Cells were pooled from 8 mice in each group and cultured in triplicate in round-bottomed microtiter wells (96 well, Nunc, Roskilde, Denmark) containing $2\times10^5$ cells in a volume of 200 μl RPMI 1640 medium supplemented with $5\times10^{-5}$ M 2-mercaptoethanol, 1 mM glutamin, penicillin-streptomycin and 5% (v/v) fetal calf serum (FCS). The mycobacterial antigens were used in concentrations ranging from 5 to 1.3 μg/ml. Culture supernatants were harvested from parallel cultures after 72h of incubation and the amount of IFN-γ was determined by ELISA as described previously (Brandt et al 1996).

Experimental Infections and Bacterial Enumeration in Organs

To evaluate the level of protection, mice were challenged ten or thirty weeks after the first immunization either by the aerosol route in a Glas-Col inhalation exposure system, calibrated to deliver approximately 100 CFUs of *M. tuberculosis* Erdman/lung or by the i.v. route with an inoculum of $5\times10^4$ CFU of *M. tuberculosis* (H37Rv) suspended in PBS in a volume of 0.2 ml. Mice were sacrificed 6 weeks (aerosol route) or 2 weeks (i.v route) later and lungs and spleens were removed for bacterial enumeration. The organs were homogenized separately in sterile saline and serial dilutions were plated onto Middelbrook 7H11 agar supplemented with 2 μg 2-thiophene-carboxylic acid hydrazide (TCH) per milliliter to selectively inhibit the growth of residual BCG in the test organs. Colonies were counted after 2–3 weeks of incubation at 37° C.

Statistical Methods

Assessment of experiments was carried out using analysis of variance. Differences between means were assessed by Tukey's test. A P value<0.05 was considered significant.

Results

Two fusion proteins, Ag85B-ESAT-6 and ESAT-6-Ag85B, were recombinantly produced in *E.coli* using the His-Tag c ion exchange chromatography and analyzed by Coomassie-stained SDS-PAGE together with the individual proteins Ag85B and ESAT-6 (FIG. 1). Western blotting, of the fusion proteins demonstrated that the proteins retained the ability to bind antibodies against either component (HYT27 and HYB76.8) (result not shown). The initial immunological investigations were done to compare the immunogenicity of the two proteins and to clarify whether both components of the fusion proteins were recognized by the immune system after processing. Groups of C57BL/6J mice were immunized with 10 µg of each fusion protein emulsified in MPL and DDA; an adjuvant combination which has recently been shown to induce a highly efficient Th1 response protective against TB (Brandt, et al 2000. Infect. Immun. 68:791–795.). As a negative control, a group of mice received the adjuvant combination alone. One week after the last injection, the mice were bled, PBMC purified and the IFN-γ release evaluated after in vitro stimulation with different concentrations of Ag85B, ESAT-6 and fusion proteins (all at 5, 2.5 and 1.3 µg/ml) (FIG. 2). Immunization with both Ag85B-ESAT-6 (panel A) and ESAT-6-Ag85B (panel B) fusion proteins induced strong IFN-γ release in response to restimulation with either fusion protein or Ag85B or ESAT-6. Immunization with the Ag85B-ESAT-6 fusion protein gave rise to the highest responses, with IFN-γ levels in the range of 45–50 ng/ml. This level of IFN-γ did not titrate out in the dose range investigated in this experiment. In another experiment, the dose interval 5–0.08 µg/ml was investigated and even with the lowest concentration (0.08 µg/ml) a significant (though lower) amount of IFN-γ (10 ng/ml) was released compared to the highest concentration (result not shown). The Ag85B-ESAT-6 fusion protein was selected for subsequent studies.

Protective Efficacy of the Fusion Protein Vaccine in the Mouse Model

Mice were immunized with Ag85B-ESAT-6 in doses ranging from 0.01 to 50 µg. A group of mice receiving the adjuvant combination alone and a group of naive mice were included as controls. Ten weeks after the first immunization, the mice received an aerosol challenge with $M.$ $tuberculosis$ Erdman. FIG. 3 shows the number of bacteria in lungs and spleens expressed as mean $\log_{10}$ CFU. Even with a dose as low as 0.01 µg, a statistical reduction in the number of bacteria was seen in the lungs (P<0.01) compared to naive controls. This was followed by a range of doses (0.1–10 µg) inducing a higher level of protection (P<0.001). There was no statistical difference between these three doses. Immunization with a dose of 50 µg was accompanied by reduced levels of protection in both organs. An immunization dose of 10 µg was the only one giving a significant level of protection in the spleen (P<0.001) and was used for subsequent studies.

We compared the protective efficacy of the fusion protein with that of a simple mix of Ag85B and ESAT-6, a ST-CF-based vaccine or BCG in two different strains of mice, C57BL/6J and B6CBAF1. The molar concentrations of Ag85B and ESAT-6 in the mixture were adjusted to be the same level as the concentrations of the two components in the fusion protein. Ten weeks after the first vaccination, the mice were challenged by the aerosol (Exp. 1 and 2) or by the i.v (Exp 3) route with virulent $M.$ $tuberculosis$. Six (Exp. 1 and 2) or two weeks (Exp. 3) post challenge, the mice were killed and the bacterial numbers were enumerated in the lungs and spleens. The vaccine-induced protection is shown in table Ia. In all three experiments the fusion protein induced high levels of protection, which was comparable to that induced by BCG. Slightly lower levels were obtained after immunizing with the mixture (Exp. 1 and Exp. 3). When compared to ESAT-6 or Ag85B administered as single components, the protective efficacy of the fusion molecule was also superior, reducing the number of bacteria by 0.3–0.4 log more than the single components in both lungs and spleens. Although the tendency was the same in all 3 experiments, a statistically significant difference was only found between Ag85B and the fusion protein in the lung in Exp. 2 (P=0.039).

Immunological Memory Induced by the Fusion Protein Vaccine

We continued by investigating whether the fusion protein vaccine induced stable immunological memory. Other groups included naive mice, BCG-vaccinated mice and a group of mice receiving the adjuvant alone. Mice were aerosol challenged with $M.$ $tuberculosis$ Erdman 10 and 30 weeks after the first vaccination. Both the fusion protein and BCG induced significant and similar levels of protection at 10 weeks (P<0.05) when compared to naive controls. The efficacy levels were similar to the previous experiment (Table Ia). The same pattern was observed after a longer rest period (30 weeks) and both vaccines induced long-lived memory immunity, which protected efficiently against tuberculosis. However, whereas the subunit vaccine promoted a stable level of protective immunity over the observation period, the efficacy of BCG had waned and induced significantly lower levels of protection in the lung than the subunit vaccine (Exp. 1 P=0.028 and Exp. 2 P=0.013). There was no significant difference between the fusion protein and BCG in the spleen (Exp. 1 P=0.956 and Exp. 2 P=0.243).

TABLE Ia

Vaccine-induced protection in the mouse model

| Vaccine group[a] | Exp. 1. C57BL/6J (H-2[b]) | | Exp. 2. C57BL/6J(H-2[b]) | | Exp. 3. B6CBAF1 (H-2[b,k]) | |
| --- | --- | --- | --- | --- | --- | --- |
| | Lung | Spleen | Lung | Spleen | Lung | Spleen |
| Naive | 5.80 ± 0.05[b] | 4.69 ± 0.14 | 5.74 ± 0.04 | 4.65 ± 0.22 | 5.44 ± 0.05 | 6.39 ± 0.03 |
| MPL-DDA | 5.91 ± 0.08 | 4.94 ± 0.07 | 5.96 ± 0.06 | 4.65 ± 0.13 | 5.13 ± 0.03 | 6.26 ± 0.09 |
| ESAT-6 | 5.44 ± 0.10 | 4.68 ± 0.18 | 5.34 ± 0.06* | 4.17 ± 0.22 | 4.48 ± 0.21*** | 6.20 ± 0.08 |
| Ag85B | 5.49 ± 0.10 | 4.43 ± 0.07 | 5.41 ± 0.06 | 4.38 ± 0.12 | 4.41 ± 0.09*** | 5.65 ± 0.11*** |
| Ag85B-ESAT-6 | 5.07 ± 0.06*** | 4.20 ± 0.09 | 5.03 ± 0.12*** | 3.72 ± 0.15** | 4.11 ± 0.15*** | 5.42 ± 0.10*** |
| Ag85B + ESAT-6 | 5.38 ± 0.08 | 4.40 ± 0.20 | ND | ND | 4.43 ± 0.12*** | 5.76 ± 0.10** |

TABLE Ia-continued

Vaccine-induced protection in the mouse model

| | Exp 1. C57BL/6J (H-2$^b$) | | Exp 2. C57BL/6J(H-2$^b$) | | Exp 3. B6CBAF1 (H-2$^{b,k}$) | |
|---|---|---|---|---|---|---|
| Vaccine group[a] | Lung | Spleen | Lung | Spleen | Lung | Spleen |
| ST-CF | 5.02 ± 0.11*** | 4.18 ± 0.11 | 4.90 ± 0.13*** | 4.09 ± 0.08 | 4.15 ± 0.11*** | 5.75 ± 0.09** |
| BCG | 5.31 ± 0.08* | 4.04 ± 0.21 | 5.18 ± 0.05** | 3.92 ± 0.12* | 4.16 ± 0.08*** | 5.39 ± 0.14*** |

[a]The mice were immunized once s.c. with BCG (5 × 10$^4$ CFU) or injected three times with the experimental vaccines emulsified in MPL-DDA.
[b]Bacterial numbers are given as mean log$_{10}$ CFU of *M. tuberculosis* ± SEM (n = 5) isolated from the spleen and lung 6 weeks post aerosol challenge (Exp. 1 and Exp. 2) and 2 weeks post i.v. challenge (Exp. 3).
*$P < 0.05$;
**$P < 0.01$;
***$P < 0.001$ when compared to naive controls.

TABLE IIa

Vaccine-induced long-term protection in the mouse model

| | | | 30 weeks | | | |
|---|---|---|---|---|---|---|
| | 10 weeks | | Exp. 1 | | Exp. 2[c] | |
| Vaccine group[a] | Lung | Spleen | Lung | Spleen | Lung | Spleen |
| Naive | 5.72 ± 0.07[b] | 4.91 ± 0.07 | 5.86 ± 0.16 | 5.05 ± 0.10 | 5.94 ± 0.08 | 5.07 ± 0.10 |
| MPL-DDA | 5.64 ± 0.05 | 5.16 ± 0.08 | 6.11 ± 0.06 | 5.30 ± 0.14 | 5.98 ± 0.10 | 4.92 ± 0.08 |
| Ag85B-ESAT-6 | 4.80 ± 0.08*** | 3.89 ± 0.16*** | 4.82 ± 0.09*** | 4.01 ± 0.36  p = 0.051 | 5.08 ± 0.09*** | 4.38 ± 0.09* |
| BCG | 4.81 ± 0.12*** | 3.74 ± 0.18*** | 5.36 ± 0.10* | 4.18 ± 0.27  p = 0.115 | 5.59 ± 0.10 | 3.97 ± 0.27*** |

[a]C57BL/6J mice were immunized once s.c. with BCG (5 × 10$^4$ CFU) or injected three times with the experimental vaccines emulsified in MPL-DDA.
[b]Bacterial numbers are given as mean log$_{10}$ CFU of *M. tuberculosis* ± SEM (n = 4–5) isolated from the spleen and lung 6 weeks post aerosol challenge.
[c]In Exp 2 the fusion protein ESAT-6-Ag85B was used for immunization.
*$P < 0.05$;
**$P < 0.01$;
***$P < 0.001$ when compared to naive controls.

EXAMPLE 5
Immune Responses Induced by Ag85B, ESAT-6 and Ag85B-ESAT-6 Fusion Protein
Animals Specific-pathogen-free female C57BL/6J (B6, H-2$^b$) mice (Bomholtegaard, Ry, Denmark) were used to evaluate proliferative responses (Table Ib) and conventional male C57BL/6/CitJ mice (Central Institute for TB, Russia) were used to assess DTH responses and protectivity of vaccines in the lethal TB model (Table IIb and FIG. 5). Outbred Dunkin Hartley guinea pigs (Charles River, Sulzfeld, Germany) were used for DTH and protection studies. All mice used were 8–16 wk of age and guinea pigs weighed approximately 250–300 g at the beginning of the experiments. Infected animals were housed in cages contained within a BL-3 laminar flow safety enclosure. Guinea pigs were weighed weekly and when they had lost 20% of their weight they were euthanised. They were also killed if displaying other signs of severe illness such as laboured breathing. The institutes (SSI and CAMR) ethical committee does not allow experiments to continue with severely diseased animals. Animals were allowed free access to water and standard mouse or guinea pig chow.
Bacteria

*M. tuberculosis* Erdman and H37Rv were grown at 37° C. in modified Sauton medium enriched with 0.5% sodium pyruvate and 0.5% glucose and in Dubos broth (Difco, Detroit, Mich.) supplemented with 0.5% BSA and oleic acid (Sigma, St. Louis, Mo.), respectively. BCG Danish 1331 used in guinea pig experiments was obtained as a freeze dried vaccine and was rehydrated with PBS. BCG Prague used in mouse experiments was grown in enriched Dubos broth, washed, suspended in sterile saline containing 0.05% Tween 20 and 0.1% BSA and stored at −80° C. until used.
Mycobacterial Antigens Short-term culture filtrate (ST-CF), recombinant ESAT-6, recombinant Ag85B and the fusion protein were produced as described previously (Andersen, P. et al 1991, Olsen, A. W. et al 2001, Harboe, M. et al 1998). Synthetic peptides as indicated in FIG. 4 were synthesized (Schafer-N, Copenhagen, Denmark).
Human T Cell Lines T cell lines were generated as described before (Ottenhoff, T. H. M. et al 1985). Briefly, peripheral blood mononuclear cells (PBMC) were obtained from HLA-DRB1-typed TB patients or individuals with documented PPD skin test conversion after contact with a case of contagious TB (PPD-converters). PMBC were incubated at 1–2×10$^6$ cells/well in 24-well plates (Nunc, Roskilde, Denmark) in the presence of ST-CF at 5 µg/ml for six days, then expanded with rIL-2. The T cell lines were then frozen and stored in liquid nitrogen. Only T cell lines that were MTB-specific, i.e. responding to MTB sonicate or purified protein derivate (PPD) (tuberculin RT23; Statens Serum Institute, Copenhagen, Denmark) but not to tetanus toxoid were used in the present study. For the analysis of antigen specific responses, T cell lines (15×10$^3$/well) were incubated with irradiated autologous or HLA-matched PBMC (50×10$^3$/ well), with or without antigen (PPD at 5 µg/ml and recombinant antigens at 0.1 and 1 µg/ml), in a total volume of 200 µl/well in triplicate in 96-well flat-bottomed microtiter plates. The proliferation was measured by [$^3$H] thymidine incorporation at day 4 and expressed as stimulation indices (SI).

Vaccination and Immunization Procedures

Mice were immunized with 10 µg of antigen emulsified with 250 µg dimethyl dioctadecylammonium bromide (DDA) (Eastman Kodak, Rochester, N.Y.) co-adjuvanted with 25 µg monophosphoryl Lipid A (MPL) (RIBI; Immunochem. Research Inc., Montana, USA). The vaccines were injected three times subcutaneously (s.c.) in the dorsum with 2-wk intervals. A single dose of live BCG Prague (106 bacilli/mouse) was injected s.c. 5 weeks before infection, no booster injections were administered. The pre-challenge immunity was evaluated by the footpad delayed-type hypersensitivity (DTH) response as previously described; Yeremeev, 2000 #95]. The recognition of the hybrid and the single components after immunization were investigated by in vitro stimulation of lymph node lymphocytes, 7 weeks after the first vaccination.

Guinea pigs were immunized with 20 µg of the Ag85B-ESAT-6 fusion protein in 500 µg DDA co-adjuvanted with 50 µg MPL. The experimental vaccines were given three times s.c. with 3 week intervals. The BCG Danish 1331 (5×104 bacilli/guinea pig) was injected s.c. once at the same time as the first vaccination. Pre-challenge immunity was evaluated by DTH responses (indurations), 4 weeks after the last vaccination as described before (5b).

Lymphocyte Cultures

Lymph node lymphocytes were pooled from 3 mice in each experiment and cultured in triplicate in round-bottomed microtiter wells (96 well, Nunc, Roskilde, Denmark) containing $2 \times 10^5$ cells in a volume of 200 µl RPMI 1640 medium supplemented with $5 \times 10^{-5}$ M 2-mercaptoethanol, 1 mM glutamine, penicillin-streptomycin and 5% (v/v) fetal calf serum (FCS). The mycobacterial antigens were all used at a concentration of 5 µg/ml. Proliferation was measured by [3H] thymidine incorporation at day 3.

Experimental Infections and Bacterial Enumeration in Organs

To evaluate long-term survival, mice were challenged intravenously 6 wk following the last immunization with a lethal dose of 5×105 CFU M. tuberculosis H37Rv. Three weeks following infection, 3 mice per group were sacrificed and CFU counts in organs were determined by plating serial 10-fold dilutions of organ homogenates onto Dubos agar dishes (Difco).

Guinea pigs were challenged 12 weeks after the initial vaccination in either a Glas-Col inhalation exposure system with M. tuberculosis Erdman (the SSI experiment 1) or using a contained Henderson apparatus (The CAMR experiment 2) as previously described (9); Williams, 2000 #108]. In both experiments did the guinea pigs receive approximately 10–20 CFUs/lung. Vaccinated and challenged guinea pigs were sacrificed 7, 13 and 17 weeks post-aerosol challenge and lungs and spleens removed aseptically. The organs were homogenized separately in sterile saline and serial dilutions were plated onto Middlebrook 7H11 agar supplemented with 2 µg 2-thiophene-carboxylic acid hydrazide (TCH) per milliliter to selectively inhibit the growth of residual BCG in the organs. Colonies were counted after 2–3 weeks of incubation at 37° C.

Results

In order to investigate if the molecular construction of the fusion protein changes the recognition of the single components and their derived epitopes, mice were vaccinated with either Ag85B, ESAT-6 or Ag85B-ESAT-6. Antigens were administered in the adjuvant DDA/MPL, recently described to induce a strong Th-1-like response against mycobacterial antigens (Brandt, L. et al 2000). Proliferative responses were tested, both to intact proteins and to peptides representing major T cell epitopes of the two antigens—Ag85B$_{241-260}$ (Yanagisawa, S. et al 1997) and ESAT-6$_{1-20}$ (Brandt, L. et al 1996). In addition, since three amino acids (NVA) were introduced between Ag85B and ESAT-6 due to the Hindlil linker (FIG. 4), peptides representing potential neo-epitopes in the linker region—Ag85$_{276-285}$NVAESAT-6$_{1-6}$ and Ag85$_{280-285}$NVAESAT-6$_{1-10}$—were synthesized and tested. The results are summarized in Table Ib. As expected, immunization with ESAT-6 elicited immune response to ESAT-6, ESAT-6$_{1-20}$ and the fusion protein, but not to Ag85B, Ag85B$_{241-260}$ or peptides covering the junction between Ag85B and ESAT-6. Similarly, immunization with Ag85B induced strong proliferative responses to Ag85B, the derived epitope Ag85B$_{241-26}$ and the fusion molecule. In this group of animals, low but detectable responses to the peptides representing the linker region were also found. Immunization with Ag85B-ESAT-6 fusion protein resulted in a strong proliferative response to both protein components, their respective epitopes and the two linker peptides. Compared to immunization with either single antigen, immunization with the Ag85B-ESAT-6 fusion protein increased the response both to ESAT-6 and Ag85B. T cell proliferative responses were generally associated with high levels of IFN-γ production (data not shown), which is in agreement with our earlier results (Olsen, A. W. et al 2001).

Protection Against Death from M. tuberculosis Infection in Ag85B-ESAT-6 Fusion Protein Vaccinated Mice We next compared the DTH response to PPD and protection conferred by the experimental vaccines and BCG in a standardized mouse survival TB model based on high dose iv challenge (Yeremeev, V. V. et al 2000, Nikonenko, B. V. et al 2000). As shown in Table IIb, vaccination with the fusion molecule and with Ag85B resulted in a prominent reduction in the lung bacterial counts compared to non-vaccinated controls (approximately 3-log 10 protection in the lung). A high level of DTH response to PPD, was also found following vaccination with these two experimental vaccines. The level of protection was similar to that conferred by a high dose of BCG (Table IIb). ESAT-6 administered alone appeared to be less effective at reducing CFUs, although it elicited a strong DTH response.

When the dynamics of mortality in vaccinated mice was assessed (FIG. 5), the protective properties of our protein vaccines were further confirmed. Non-vaccinated control mice succumbed to infection with a mean survival time (MST) of 28.0±2.2 days, which is in good agreement with our previous reports (Yeremeev, V. V. et al 2000, Abou-Zeid, C. et al 1997). No difference in the MST between mice vaccinated with adjuvant alone and PBS was found (data not shown). All vaccines significantly prolonged survival, however, large differences between individual vaccines were found. Administration of ESAT-6 increased the MST by a factor of two compared to controls (64.3±9.0 and 28.0±2.2 days). Efficient protection was provided by the vaccines based on Ag85B (MST=84.2±8.6 days) and especially the fusion protein (MST=119.1±17.7 days), although none of these vaccines fully achieved the level of protection with BCG (MST=159.4±19.0 days).

Evaluation of the Ag85B-ESAT-6 fusion protein vaccine in the guinea pig model We continued by evaluating if the fusion protein-based vaccine was able to confer protection in the highly susceptible aerosol-infection guinea pig model. As shown in table lllb, the DTH response of animals vaccinated with BCG was predominantly to PPD, with only minimal response to the fusion protein. Vaccination with the fusion protein, on the other hand, induced a strong DTH response to the fusion protein and a lower response to PPD. When the bacterial loads in lungs and spleens were measured at week 7 post-infection, the highest level of protection was seen in the BCG-vaccinated group (about 2 $\log_{10}$ and 1.5 $\log_{10}$ reduction in numbers of bacteria in spleens and lungs, respectively, compared to the adjuvant-inoculated control, Table IIIb, Exp 1). Vaccination with the Ag85B-ESAT-6 fusion protein conferred a 1$\log_{10}$ reduction in bacterial numbers in the spleen. In the lung, the difference between vaccinated and control group was less pronounced (5-fold reduction, statistically not significant). Interestingly, at week 13 post infection a comparison between the BCG and Ag85B-ESAT-6 vaccinated groups (the control animals had been euthanized at this time-point due to the development of severe clinical disease), revealed no significant difference in the bacterial numbers in the spleen whereas the BCG group still had fewer bacterial numbers in the lung at this time-point. Severe loss of body weight, or wasting, is a common and well-described clinical symptom in tuberculosis patients (Prout, S. et al 1980). Hence, we monitored the body weight as a potentially important parameter of *M. tuberculosis*-triggered disease in guinea pigs (FIG. 6). When the guinea pigs had lost 20% of maximum weight or, if showing other signs of severe illness they were euthanized. Non-vaccinated control guinea pigs began to lose weight about 40 days post challenge (FIG. 6A). 20 days later two of the guinea pigs were killed and three more were killed between day 80 and 120. Only one guinea pig from the control group appeared healthy when the study was terminated. Animals vaccinated with BCG all increased in weight and appeared healthy throughout the study period (FIG. 6B). Animals given the fusion protein all gained weight until 70 days post challenge. At this point, one guinea pig started to lose weight and was killed 30 days later. The remaining guinea pigs in the fusion protein group still appeared healthy when the study was terminated at 17 weeks post-challenge (FIG. 6C). In FIG. 6D the data has been given as survival curves for the three different vaccines. Organs were taken from the surviving guinea pigs and the bacterial loads in lungs and spleens were determined (Table IIIb, Exp. 2). No difference in the bacterial numbers in the spleen was found between BCG and fusion protein-vaccinated groups of animals and at this late time-point only few bacteria could be recovered from this organ. The BCG group still had significantly less bacteria in the lung at this time-point.

The Ag85B-ESAT-6 fusion protein is recognized by T cells of various HLA types To investigate if the fusion protein is broadly recognized by donors of different HLA type, we tested T cell lines derived from 7 TB patients and 2 PPD-converters representing 8 different HLA-DR phenotypes. The T cell lines raised against *M. tuberculosis* were tested with respect to their ability to specifically proliferate in the presence of ESAT-6, Ag85B and the fusion protein. As shown in FIG. 7, eight out of nine T cell lines tested, proliferated vigorously in response to the fusion protein, and this response largely paralleled that of ESAT-6. A response to Ag85B was only seen in a few donors, was always lower and did not increase at higher antigen concentrations (data not shown). Only one PPD-responsive T cell line was non-responsive to the fusion protein. Thus the Ag85-ESAT-6 protein is broadly recognized by human T cells in the context of many different HLA backgrounds.

TABLE Ib

Proliferative responses by lymph node lymphocytes isolated from mice vaccinated with Ag85B-ESAT-6

Proliferative response (CPM × 10³)[a] with the following antigens:

| Immunogen[b] | None | Ag85B-ESAT-6 | ESAT-6 | ESAT-6$_{1-20}$ | Ag85B | Ag85B$_{241-260}$ | Ag85B$_{276-285}$-NVAESAT-6$_{1-6}$ | Ag85B$_{280-285}$ NVAESAT-6$_{1-10}$ |
|---|---|---|---|---|---|---|---|---|
| ESAT-6 | 3.41 ± 0.74[c] | 11.26 ± 1.27 | 13.00 ± 2.34 | 7.97 ± 1.97 | 1.72 ± 0.08 | 2.68 ± 0.08 | 2.91 ± 0.62 | 2.21 ± 0.01 |
| Ag85B | 2.43 ± 0.01 | 20.04 ± 2.49 | 3.93 ± 0.29 | 4.68 ± 0.25 | 12.46 ± 1.71 | 13.57 ± 2.27 | 6.91 ± 0.53 | 4.79 ± 0.36 |
| Ag85B-ESAT-6 | 3.49 ± 0.17 | 41.67 ± 1.99 | 18.05 ± 2.70 | 28.59 ± 1.81 | 23.04 ± 0.72 | 32.98 ± 0.91 | 18.87 ± 0.38 | 15.93 ± 1.22 |

[a]Three weeks after the last booster injection the proliferative responses were measured in lymph node lymphocyte cultures.
[b]The mice were immunized s.c. three times with the experimental vaccines emulsified in MPL-DDA.
[c]Values are expressed as mean CPM × 103 ± SEM of triplicate analyses performed on cells pooled from three mice. The experiment has been repeated with similar results.

TABLE IIb

DTH response (footpad swelling) in vaccinated mice and CFU counts in vaccinated and infected mice

| Immunogen[a] | DTH ± SEM[b] | CFU (lung)[c] | CFU (spleen) |
|---|---|---|---|
| Control | 0.10 ± 0.02 | (9.8 ± 4.9) × 10$^9$ | (5.5 ± 2.0) × 10$^7$ |
| BCG Prague (10$^6$) | 0.48 ± 0.06 | (1.4 ± 0.5) × 10$^6$ | (1.1 ± 0.2) × 10$^5$ |

TABLE IIb-continued

DTH response (footpad swelling) in vaccinated mice and CFU counts in vaccinated and infected mice

| Immunogen[a] | DTH ± SEM[b] | CFU (lung)[c] | CFU (spleen) |
|---|---|---|---|
| ESAT-6 | 0.50 ± 0.08 | $(8.2 ± 1.5) \times 10^7$ | $(8.1 ± 2.0) \times 10^6$ |
| Ag85B | 0.52 ± 0.09 | $(3.6 ± 1.7) \times 10^6$ | $(2.7 ± 0.2) \times 10^6$ |
| Ag85B-ESAT-6 | 0.75 ± 0.12 | $(3.5 ± 1.5) \times 10^6$ | $(2.8 ± 1.0) \times 10^6$ |

[a]Mice were vaccinated once with $10^6$ CFU of BCG or injected three times with experimental protein vaccines emulsified in MPL-DDA.
[b]DTH response to PPD is expressed in millimeters as mean footpad swelling ± SEM (n = 15) at week 3 following the 3rd immunization.
[c]Bacterial numbers ± SEM (n = 3) in lungs and spleens at week 3 following H37Rv challenge.

TABLE IIIb

DTH responses and vaccine-induced protection in the guinea pig model

| | DTH responses | | Exp. 1 | | | | Exp. 2[e] | |
|---|---|---|---|---|---|---|---|---|
| | (diameter of induration in mm)[b] | | $Log_{10}$ mean | $Log_{10}$ mean | $Log_{10}$ mean | $Log_{10}$ mean | $Log_{10}$ mean | $Log_{10}$ mean |
| Vaccine group[a] | PPD | Ag85B-ESAT-6 | CFU (lung)[c] 7 weeks | CFU (spleen) 7 weeks | CFU (lung) 13 weeks | CFU (spleen) 13 weeks | CFU (lung) 17 weeks | CFU (spleen) 17 weeks |
| BCG | 11.2 ± 1.4 | 5.1 ± 3.4 | 3.98 ± 0.11** | 3.70 ± 0.24* | 4.86 ± 0.54 | 4.79 ± 0.58 | 5.51 ± 0.19 | 2.83 ± 0.22 |
| Adjuvant | 6.1 ± 3.0 | 4.6 ± 2.7 | 5.45 ± 0.30 | 5.65 ± 0.40 | NA[d] | NA | NA | NA |
| Ag85B-ESAT-6 | 9.1 ± 1.5 | 13.0 ± 1.5 | 5.09 ± 0.21 | 4.68 ± 0.32* | 5.76 ± 0.15 | 4.72 ± 0.42 | 6.42 ± 0.25 | 2.70 ± 0.54 |

[a]Guinea pigs were immunized once s.c. with $5 \times 10^4$ CFU of BCG or injected three times s.c. with the experimental vaccine emulsified in MPL-DDA and sacrificed in the beginning of week 7 and 13 (Exp. 1) or week 17 (Exp. 2) post challenge.
[b]DTH responses were read after 24 h, expressed as mean diameter of induration ± SEM (n = 5) and responses larger than 5 mm were regarded positive. Responses to PBS were less than 5 mm.
[c]Bacterial numbers are given as mean $log_{10}$ CFU of M. tuberculosis ± SEM (n = 5–6) isolated from the spleen and lung.
[d]NA, not available, due to severe disease, they were euthanised before week 13.
[e]In Exp. 2 guinea pigs injected with saline instead of adjuvant were used as controls. One Way Analysis of variance followed by Tukey's test was used to test the effects of vaccination.
*P < 0.05;
**P < 0.01.

EXAMPLE 6

The course of disease after intratracheal infection of cynomologus monkeys was assessed in non-vaccinate or BCG-vaccinated animals and compared to the effect of vaccination with a subunit vaccine (Ag85b-ESAT-6 fusion) in a DDA/MPL-containing adjuvant. Experiments used 3 animals per experimental group. During vaccination and infection, PBMC and serum were routinely collected and alveolar cells obtained by bronchoalveolar lavage. The development and specificity of cellular responses (IFN-γ production) in response to mycobacterial antigens was assessed before and after vaccination. Peripheral and local immune responses were correlated with the course of disease (general behaviour, coughing, weight, ESR, CRP, serology, skin testing and X-ray) and gross pathology (detailed immunohistopathology of lungs and other organs and observation of local cellular responses as well as determination of bacterial load determined by necropsy).

Results from the first round of experiments show induction of antigen-specific IFN-γ production to subsequent in vitro rechallenge of lymphocytes with the vaccine. Vaccinated animals show significant protection against aerosol infection with M. tuberculosis as well as reduced pathology and weight loss, see FIGS. 8–10.

References

Abou-Zeid, C. et al 1997. Infect Immun. 65:1856.
Anacker, R. L. et al 1967. J.Immunol. 98:1265–1273.
Andersen, P. 1994. Infect.Immun. 62:2536–2544.
Andersen, P. et al 1991. Infect. Immun. 59:1905.
Andersen, P., and Heron, 1. 1993 J. Immunol. Methods 161 29–39
Baldwin, S. L. et al 1998. Infect.Immun. 66:2951–2959
Boesen, H. et al 1995. Infect.Immun. 63:1491–1497.
Brandt et al 1996. J.Immunol. 157:3527–3533.
Brandt, L. et al 2000. Infect. Immun. 68:791–795.
Cole, S. T et al 1998 Nature 393:537–544
Cote-Sierra J, et al 1998, Gene Oct 9;221(1):25–34
Delogu et al 2000. Infect. Immun. 68:3097–102.
Dillon et al 1999. Infect.Immun. 67:2941–2950.
Dobos, K. M. et al 1996. J.Bacteriol. 178:2498–2506.
Gosselin et al 1992 J.Immunol. 149; 3477–3481
Guleria et al 1996. Nat.Med. 2:334–337.
Harboe, M., et al 1998 Infect.Immun. 66:2; 717–723
Horwitz et al 1995. Proc.Natl.Acad.Sci.U.S.A. 92:1530–1534.
Huygen et al 1996. Nat.Med. 2:893–898.
Kilgus J et al, J.Immunol. 1991 Jan 1;146(1):307–15.
Li, Z et al. 1999. Infect.Immun. 67:4780–4786.
Lowry, D. B. et al 1999, Nature 400:269–71
Nagai et al 1991, Infect. Immun 59:1; 372–382
Nikonenko, B. V. et al 2000. Tuber. Lung Dis. 80:15.
Olsen A. W et al, Eur J Immunol. 2000 Jun; 30(6):1724–3
Olsen, A. W. et al 2001. Infect. Immun. In press
Orme, I. M. 1988. Infect.Immun. 56:3310–3312.
Orme, I. M. et al 1993. J.lnfect.Dis. 167:1481–1497.
Ottenhoff, T. H. M. et al 1985. Hum. Immunol. 13:105.
Patent application PA 2000 00666 (our ref. 22030 DK1) "Nucleic acid fragments and polypeptide fragments derived from M. tuberculosis"
Patent application U.S. Ser. No. 09/0505,739 "Nucleic acid fragments and polypeptide fragments derived from M. tuberculosis"
Patent application WO 01/04151 (our ref.23388 DK1) "Tuberculosis vaccine and diagnostic based on the Mycobacterium tuberculosis esat-6 gene family".
Pathan, A. et al 1998. Immunity to Infection. 95:90.
Pollock. J., et al, 2000. The Veterinary record, 146:659–665

Prout, S. et al 1980. S Afr. Med. J. 58:835.
Ravn, P. et al 1999. J.Infect.Dis. 179:637–645.
Roberts, A. D. et al 1995. Immunology. 85:502–508.
Roche, P. W. et al 1994. Infect.Immun. 62:5319–5326.
Rolph, M. S, and I. A. Ramshaw. 1997. Curr.Opin.Immunol. 9:517–24
Rosenkrands, I., et al 1998, Infect. Immun 66:6; 2728–2735
Sambrook et al (Molecular Cloning; A laboratory manual, Cold Spring Harbor Laboratories, NY, 1989
Sinigaglia F et al. Nature 1988 Dec 22–29;336(6201):778–80
Skjøt, R. L. V., et al 2000, Infect. Immun 68:1; 214–220
Sorensen, A. L. et al 1995. 63:1710–1717.
Stryhn, A., et 1996 Eur. J. Immunol. 26:1911–1918
Tascon et al 1996. Nat.Med. 2:888–892.
Thompson J., et al Nucleic Acids Res 1994 22:4673–4680
Ulmer J. B et al 1993, Curr. Opin. Invest. Drugs 2(9): 983–989
Ulrichs, T. et al 1998.Eur.J.Immunol. 28:3949–3958.
Webb, J. R. et al 1998. Infect.Immun. 66:4208–4214.
Wiegeshaus, E. H. et al 1970. Am. Rev. Respir. Dis. 102:422.
Yanagisawa, S. et al 1997. Int. Immunol. 9:227.
Yeremeev, V. V. et al 2000. Clin. Exp. Immunol. 120:274.

What is claimed is:

1. A polypeptide selected from the group consisting of
   (a) a fusion polypeptide which comprises a first amino acid sequence including at least one stretch of amino acids constituting a T-cell epitope from the *M. tuberculosis* protein ESAT-6 comprising at least 6 amino acids of SEQ ID NO: 1 and a second amino acid sequence including at least one stretch of amino acids constituting a T-cell epitope from the *M. tuberculosis* protein Ag85B comprising at least 6 amino acids of SEQ ID NO: 2 said first and second amino acid sequences optionally being fused via a linker sequence;
   (b) a polypeptide comprising an amino acid sequence analogue having at least 70% sequence identity to the sequence in (a) and at the same time being immunogenic; and
   (c) a fusion polypeptide which comprises a first amino acid sequence having at least 70% sequence identity to the first amino acid sequence in (a) and at the same time being immunogenic, and a second amino acid sequence having at least 70% sequence identity to the second amino acid sequence in (a) and at the same time being immunogenic, said first and second amino acid sequences optionally being fused via a linker sequence.

2. A polypeptide according to claim 1, wherein the degree of sequence identity is at least 75%.

3. A polypeptide according to claim 1, wherein the first amino acid sequence is situated C-terminally to the second amino acid sequence.

4. A polypeptide according to claim 1, wherein the fist amino acid sequence is situated N-terminally to the second amino acid sequence.

5. A polypeptide according to claim 1, wherein no linkers are introduced between the two amino acid sequences in (a) or (c).

6. A polypeptide according to claim 1, which is Ag85B fused N- or C-terminally to ESAT-6.

7. A polypeptide according to claim 1, which is lipidated so as to allow a self-adjuvating effect of the polypeptide.

8. A method for preparing a pharmaceutical composition for the vaccination against infections caused by *Mycobacterium tuberculosis*, said method comprising preparing, synthesizing or isolating a polypeptide according to claim 1.

9. An immunogenic composition comprising a polypeptide according to claim 1.

10. An immunogenic composition according to claim 9, which is in the form of a vaccine against *Mycobacterium tuberculosis*.

11. A method for producing a polypeptide according to claim 1, comprising
    (a) inserting a nucleic acid fragment comprising a nucleic acid sequence that encodes a polypeptide as defined in claim 1, or comprising a nucleic acid sequence complementary thereto, into a vector which is able to replicate in a host cell, introducing the resulting recombinant vector into the host cell, culturing the host cell in a culture medium under conditions sufficient to effect expression of the polypeptide, and recovering the polypeptide from the host cell or culture medium;
    (b) isolating Ag85B and ESAT-6 from *Mycobacterium tuberculosis, Mycobacterium africanum* or *Mycobacterium bovis*, from culture filtrate or from lysates or fractions thereof, and fusing the polypeptides;
    (c) synthesizing the polypeptide by solid or liquid phase peptide synthesis; or
    (d) a combination of the methods in (a), (b) and/or (c).

12. A pharmaceutical composition comprising a polypeptide according to claim 1.

13. A method for producing a polypeptide according to claim 1, comprising
    (a) inserting a nucleic acid fragment which comprises a nucleic acid sequence which encodes the polypeptide, or which comprises a nucleic acid sequence complementary thereinto a vector which is able to replicate in a host cell, introducing the resulting recombinant vector into the host cell, culturing the host cell in a culture medium under conditions sufficient to effect expression of the polypeptide, and recovering the polypeptide from the host cell or culture medium; or
    (b) isolating Ag85B and ESAT-6 from a whole mycobacterium, from culture filtrate or from lysates or fractions thereof, and fusing the polypeptides;
    (c) synthesizing the polypeptide by solid-phase or liquid-phase peptide synthesis; or
    (d) a combination of the methods in (a), (b), and/or (c).

14. The method of claim 13 wherein the mycobacterium is *Mycobacterium tuberculosis, Mycobacterium africanum,* or *Mycobacterium bovis*.

15. The polypeptide according to claim 1 which contains a T-cell epitope of ESAT-6 and a T-cell epitope of Ag85B.

16. A polypeptide comprising a fusion polypeptide which comprises a first amino acid sequence including at least one stretch of amino acids constituting a T-cell epitope from the *M. tuberculosis* protein ESAT-6 comprising at least 6 amino acids of SEQ ID NO: 1 and a second amino acid sequence including at least one stretch of amino acids constituting a T-cell epitope from the *M. tuberculosis* protein Ag85B comprising at least 6 amino acids of SEQ ID NO: 2 wherein AG85B is fused N- or C-terminally to ESAT-6.

17. The polypeptide of claim 16, wherein Ag85B is fused C-terminally to ESAT-6.

18. The polypeptide of claim 17, wherein the polypeptide is ESAT-6-Ag85B.

19. An immunogenic composition comprising the polypeptide of claim 16.

20. An immunogenic composition comprising the polypeptide of claim 17.

21. An immunogenic composition comprising the polypeptide of claim 18.

* * * * *

UNITED STATES PATENT AND TRADEMARK OFFICE
CERTIFICATE OF CORRECTION

PATENT NO. : 7,037,510 B2 Page 1 of 1
APPLICATION NO. : 09/805,427
DATED : May 2, 2006
INVENTOR(S) : Peter Anderson et al.

It is certified that error appears in the above-identified patent and that said Letters Patent is hereby corrected as shown below:

Column 45, Claim 4, line 31　　A polypeptide according to claim 1, wherein the delete "fist" add first.

Signed and Sealed this

Fifteenth Day of August, 2006

JON W. DUDAS
*Director of the United States Patent and Trademark Office*

SEQUENCE LISTING

<160> NUMBER OF SEQ ID NOS: 12

<210> SEQ ID NO 1
<211> LENGTH: 95
<212> TYPE: PRT
<213> ORGANISM: Mycobacterium tuberculosis

<400> SEQUENCE: 1

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 2
<211> LENGTH: 325
<212> TYPE: PRT
<213> ORGANISM: Mycobacterium tuberculosis
<220> FEATURE:
<221> NAME/KEY: SIGNAL
<222> LOCATION: (1)..(40)

<400> SEQUENCE: 2

Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
        35                  40                  45

Glu Tyr Leu Gln Val Pro Ser Pro Ser Met Gly Arg Asp Ile Lys Val
    50                  55                  60

Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
                100                 105                 110

Gly Gly Gln Ser Ser Phe Tyr Ser Asp Trp Tyr Ser Pro Ala Cys Gly

```
            115                 120                 125
Lys Ala Gly Cys Gln Thr Tyr Lys Trp Glu Thr Phe Leu Thr Ser Glu
    130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
        195                 200                 205

Gly Asp Ala Gly Gly Tyr Lys Ala Ala Asp Met Trp Gly Pro Ser Ser
    210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
        275                 280                 285

Gly His Asn Ala Val Phe Asn Phe Pro Pro Asn Gly Thr His Ser Trp
    290                 295                 300

Glu Tyr Trp Gly Ala Gln Leu Asn Ala Met Lys Gly Asp Leu Gln Ser
305                 310                 315                 320

Ser Leu Gly Ala Gly
                325

<210> SEQ ID NO 3
<211> LENGTH: 404
<212> TYPE: PRT
<213> ORGANISM: Artificial Sequence
<220> FEATURE:
<223> OTHER INFORMATION: Recombinant Fusion protein Ag85B-ESAT-6

<400> SEQUENCE: 3

Met Ala Thr Val Asn Arg Ser Arg His His His His His His His
1               5                   10                  15

Ile Glu Gly Arg Ser Phe Ser Arg Pro Gly Leu Pro Val Glu Tyr Leu
            20                  25                  30

Gln Val Pro Ser Pro Ser Met Gly Arg Asp Ile Lys Val Gln Phe Gln
        35                  40                  45

Ser Gly Gly Asn Ser Pro Ala Val Tyr Leu Leu Asp Gly Leu Arg
    50                  55                  60

Ala Gln Asp Asp Tyr Asn Gly Trp Asp Ile Asn Thr Pro Ala Phe Glu
65                  70                  75                  80

Trp Tyr Tyr Gln Ser Gly Leu Ser Ile Val Met Pro Val Gly Gly Gln
                85                  90                  95

Ser Ser Phe Tyr Ser Asp Trp Tyr Ser Pro Ala Cys Gly Lys Ala Gly
            100                 105                 110

Cys Gln Thr Tyr Lys Trp Glu Thr Phe Leu Thr Ser Glu Leu Pro Gln
        115                 120                 125

Trp Leu Ser Ala Asn Arg Ala Val Lys Pro Thr Gly Ser Ala Ala Ile
    130                 135                 140

Gly Leu Ser Met Ala Gly Ser Ser Ala Met Ile Leu Ala Ala Tyr His
```

-continued

```
           145                 150                 155                 160
Pro Gln Gln Phe Ile Tyr Ala Gly Ser Leu Ser Ala Leu Leu Asp Pro
                165                 170                 175

Ser Gln Gly Met Gly Pro Ser Leu Ile Gly Leu Ala Met Gly Asp Ala
                180                 185                 190

Gly Gly Tyr Lys Ala Ala Asp Met Trp Gly Pro Ser Ser Asp Pro Ala
                195                 200                 205

Trp Glu Arg Asn Asp Pro Thr Gln Gln Ile Pro Lys Leu Val Ala Asn
        210                 215                 220

Asn Thr Arg Leu Trp Val Tyr Cys Gly Asn Gly Thr Pro Asn Glu Leu
225                 230                 235                 240

Gly Gly Ala Asn Ile Pro Ala Glu Phe Leu Glu Asn Phe Val Arg Ser
                245                 250                 255

Ser Asn Leu Lys Phe Gln Asp Ala Tyr Asn Ala Ala Gly Gly His Asn
                260                 265                 270

Ala Val Phe Asn Phe Pro Pro Asn Gly Thr His Ser Trp Glu Tyr Trp
                275                 280                 285

Gly Ala Gln Leu Asn Ala Met Lys Gly Asp Leu Gln Ser Ser Leu Gly
        290                 295                 300

Ala Gly Lys Leu Ala Met Thr Glu Gln Gln Trp Asn Phe Ala Gly Ile
305                 310                 315                 320

Glu Ala Ala Ala Ser Ala Ile Gln Gly Asn Val Thr Ser Ile His Ser
                325                 330                 335

Leu Leu Asp Glu Gly Lys Gln Ser Leu Thr Lys Leu Ala Ala Ala Trp
                340                 345                 350

Gly Gly Ser Gly Ser Glu Ala Tyr Gln Gly Val Gln Gln Lys Trp Asp
                355                 360                 365

Ala Thr Ala Thr Glu Leu Asn Asn Ala Leu Gln Asn Leu Ala Arg Thr
        370                 375                 380

Ile Ser Glu Ala Gly Gln Ala Met Ala Ser Thr Glu Gly Asn Val Thr
385                 390                 395                 400

Gly Met Phe Ala

<210> SEQ ID NO 4
<211> LENGTH: 403
<212> TYPE: PRT
<213> ORGANISM: Artificial Sequence
<220> FEATURE:
<223> OTHER INFORMATION: Recombinant Fusion protein ESAT-6-Ag85B

<400> SEQUENCE: 4

Met Ala Thr Val Asn Arg Ser Arg His His His His His His
1               5                  10                  15

Ile Glu Gly Arg Ser Met Thr Glu Gln Gln Trp Asn Phe Ala Gly Ile
                20                  25                  30

Glu Ala Ala Ala Ser Ala Ile Gln Gly Asn Val Thr Ser Ile His Ser
                35                  40                  45

Leu Leu Asp Glu Gly Lys Gln Ser Leu Thr Lys Leu Ala Ala Ala Trp
        50                  55                  60

Gly Gly Ser Gly Ser Glu Ala Tyr Gln Gly Val Gln Gln Lys Trp Asp
65                  70                  75                  80

Ala Thr Ala Thr Glu Leu Asn Asn Ala Leu Gln Asn Leu Ala Arg Thr
                85                  90                  95

Ile Ser Glu Ala Gly Gln Ala Met Ala Ser Thr Glu Gly Asn Val Thr
                100                 105                 110
```

Gly Met Phe Ala Lys Leu Phe Ser Arg Pro Gly Leu Pro Val Glu Tyr
                115                 120                 125

Leu Gln Val Pro Ser Pro Ser Met Gly Arg Asp Ile Lys Val Gln Phe
130                 135                 140

Gln Ser Gly Gly Asn Asn Ser Pro Ala Val Tyr Leu Leu Asp Gly Leu
145                 150                 155                 160

Arg Ala Gln Asp Asp Tyr Asn Gly Trp Asp Ile Asn Thr Pro Ala Phe
                165                 170                 175

Glu Trp Tyr Tyr Gln Ser Gly Leu Ser Ile Val Met Pro Val Gly Gly
                180                 185                 190

Gln Ser Ser Phe Tyr Ser Asp Trp Tyr Ser Pro Ala Cys Gly Lys Ala
                195                 200                 205

Gly Cys Gln Thr Tyr Lys Trp Glu Thr Phe Leu Thr Ser Glu Leu Pro
                210                 215                 220

Gln Trp Leu Ser Ala Asn Arg Ala Val Lys Pro Thr Gly Ser Ala Ala
225                 230                 235                 240

Ile Gly Leu Ser Met Ala Gly Ser Ser Ala Met Ile Leu Ala Ala Tyr
                245                 250                 255

His Pro Gln Gln Phe Ile Tyr Ala Gly Ser Leu Ser Ala Leu Leu Asp
                260                 265                 270

Pro Ser Gln Gly Met Gly Pro Ser Leu Ile Gly Leu Ala Met Gly Asp
                275                 280                 285

Ala Gly Gly Tyr Lys Ala Ala Asp Met Trp Gly Pro Ser Ser Asp Pro
290                 295                 300

Ala Trp Glu Arg Asn Asp Pro Thr Gln Gln Ile Pro Lys Leu Val Ala
305                 310                 315                 320

Asn Asn Thr Arg Leu Trp Val Tyr Cys Gly Asn Gly Thr Pro Asn Glu
                325                 330                 335

Leu Gly Gly Ala Asn Ile Pro Ala Glu Phe Leu Glu Asn Phe Val Arg
                340                 345                 350

Ser Ser Asn Leu Lys Phe Gln Asp Ala Tyr Asn Ala Ala Gly Gly His
                355                 360                 365

Asn Ala Val Phe Asn Phe Pro Pro Asn Gly Thr His Ser Trp Glu Tyr
370                 375                 380

Trp Gly Ala Gln Leu Asn Ala Met Lys Gly Asp Leu Gln Ser Ser Leu
385                 390                 395                 400

Gly Ala Gly

<210> SEQ ID NO 5
<211> LENGTH: 36
<212> TYPE: DNA
<213> ORGANISM: Artificial Sequence
<220> FEATURE:
<223> OTHER INFORMATION: Primer OPBR-4

<400> SEQUENCE: 5
ggcgccggca agcttgccat gacagagcag cagtgg                          36

<210> SEQ ID NO 6
<211> LENGTH: 26
<212> TYPE: DNA
<213> ORGANISM: Artificial Sequence
<220> FEATURE:
<223> OTHER INFORMATION: Primer OPBR-28

<400> SEQUENCE: 6

```
cgaactcgcc ggatcccgtg tttcgc                                    26
```

<210> SEQ ID NO 7
<211> LENGTH: 32
<212> TYPE: DNA
<213> ORGANISM: Artificial Sequence
<220> FEATURE:
<223> OTHER INFORMATION: Primer OPBR-48

<400> SEQUENCE: 7

```
ggcaaccgcg agatctttct cccggccggg gc                             32
```

<210> SEQ ID NO 8
<211> LENGTH: 27
<212> TYPE: DNA
<213> ORGANISM: Artificial Sequence
<220> FEATURE:
<223> OTHER INFORMATION: Primer OPBR-3

<400> SEQUENCE: 8

```
ggcaagcttg ccggcgccta acgaact                                   27
```

<210> SEQ ID NO 9
<211> LENGTH: 30
<212> TYPE: DNA
<213> ORGANISM: Artificial Sequence
<220> FEATURE:
<223> OTHER INFORMATION: Primer OPBR-75

<400> SEQUENCE: 9

```
ggacccagat ctatgacaga gcagcagtgg                                30
```

<210> SEQ ID NO 10
<211> LENGTH: 47
<212> TYPE: DNA
<213> ORGANISM: Artificial Sequence
<220> FEATURE:
<223> OTHER INFORMATION: Primer OPBR-76

<400> SEQUENCE: 10

```
ccggcagccc cggccgggag aaaagctttg cgaacatccc agtgacg             47
```

<210> SEQ ID NO 11
<211> LENGTH: 44
<212> TYPE: DNA
<213> ORGANISM: Artificial Sequence
<220> FEATURE:
<223> OTHER INFORMATION: Primer OPBR-77

<400> SEQUENCE: 11

```
gttcgcaaag cttttctccc ggccggggct gccggtcgag tacc                44
```

<210> SEQ ID NO 12
<211> LENGTH: 20
<212> TYPE: DNA
<213> ORGANISM: Artificial Sequence
<220> FEATURE:
<223> OTHER INFORMATION: Primer OPBR-18

<400> SEQUENCE: 12

```
ccttcggtgg atcccgtcag                                           20
```